US010864006B2

(12) United States Patent
Tillman et al.

(10) Patent No.: US 10,864,006 B2
(45) Date of Patent: Dec. 15, 2020

(54) ADJUSTABLE LENGTH LAPAROSCOPIC INSTRUMENT

(71) Applicant: CareFusion 2200, Inc., San Diego, CA (US)

(72) Inventors: Sara Tillman, Vernon Hills, IL (US); Andrew VanDeWeghe, Grayslake, IL (US); Bradley Thomas Williams, Round Lake Beach, IL (US); Joanna Rosenbaum, Chicago, IL (US); Timothy Hussey, Chicago, IL (US); Jessica McQuaide, Morristown, NJ (US); Thomas Wilschke, Chicago, IL (US); Jason Cartwright, Libertyville, IL (US)

(73) Assignee: CareFusion 2200, Inc., San Diego, CA (US)

( * ) Notice: Subject to any disclaimer, the term of this patent is extended or adjusted under 35 U.S.C. 154(b) by 431 days.

(21) Appl. No.: 15/692,011

(22) Filed: Aug. 31, 2017

(65) Prior Publication Data
US 2019/0059923 A1    Feb. 28, 2019

(51) Int. Cl.
*A61B 17/29* (2006.01)
*A61B 18/08* (2006.01)
(Continued)

(52) U.S. Cl.
CPC .......... *A61B 17/2909* (2013.01); *A61B 17/29* (2013.01); *A61B 18/085* (2013.01);
(Continued)

(58) Field of Classification Search
CPC .......... A61B 2017/00991; A61B 2018/00196; A61B 2017/2901; A61B 17/3201;
(Continued)

(56) References Cited

U.S. PATENT DOCUMENTS 5,511,564 A    4/1996 Wilk
5,578,052 A    11/1996 Koros et al.
(Continued)

FOREIGN PATENT DOCUMENTS

EP            3254629 A1    12/2017
WO    WO-2016045049 A1 *  3/2016  ........ A61B 17/2909
(Continued)

OTHER PUBLICATIONS

International Search Report and Written Opinion relating to International Application No. PCT/US2018/047047 dated Nov. 8, 2018.

*Primary Examiner* — Shaun L David
*Assistant Examiner* — Christina C Lauer
(74) *Attorney, Agent, or Firm* — Dinsmore & Shohl LLP

(57) ABSTRACT

An adjustable length laparoscopic instrument is provided. The instrument includes a shaft with a shaft distal end and a shaft proximal end. The instrument further includes an actuation rod with an actuation rode distal end and an actuation rod proximal end. The actuation rod is receivable by the shaft such that the actuation rod can translate longitudinally relative to the shaft to actuate an end effector. The instrument further includes a handle configured to hold the shaft and the actuation rod. The handle is configured to cause the actuation rod to translate longitudinally relative to the shaft to actuate the end effector. The instrument further includes a length adjustment mechanism configured to adjust a shaft length. The shaft length is defined between the handle and the shaft distal end.

12 Claims, 21 Drawing Sheets

(51) Int. Cl.
  *A61B 18/14* (2006.01)
  *A61B 17/34* (2006.01)
  *A61B 17/3201* (2006.01)
  *A61B 18/00* (2006.01)
  *A61B 17/00* (2006.01)

(52) U.S. Cl.
  CPC ...... *A61B 18/1445* (2013.01); *A61B 17/3201* (2013.01); *A61B 17/3417* (2013.01); *A61B 2017/00991* (2013.01); *A61B 2017/2901* (2013.01); *A61B 2017/2902* (2013.01); *A61B 2018/00053* (2013.01); *A61B 2018/00196* (2013.01)

(58) Field of Classification Search
  CPC ... A61B 17/29; A61B 17/2909; A61B 18/085; A61B 2017/2923
  See application file for complete search history.

(56) References Cited

U.S. PATENT DOCUMENTS

| | | |
|---|---|---|
| 5,766,167 A | 6/1998 | Eggers et al. |
| 8,025,621 B2 | 9/2011 | Ewaschuk et al. |
| 8,986,287 B2 | 3/2015 | Park et al. |
| 2007/0093790 A1* | 4/2007 | Downey .......... A61B 17/00234 606/1 |
| 2007/0175951 A1* | 8/2007 | Shelton, IV ..... A61B 17/07207 227/176.1 |
| 2015/0094612 A1 | 4/2015 | Miyazaki et al. |
| 2016/0008063 A1 | 1/2016 | Wake |
| 2016/0100858 A1 | 4/2016 | Flom |

FOREIGN PATENT DOCUMENTS

| WO | WO2016045049 A1 | 3/2016 |
|---|---|---|
| WO | WO2016125375 A1 | 8/2016 |

* cited by examiner

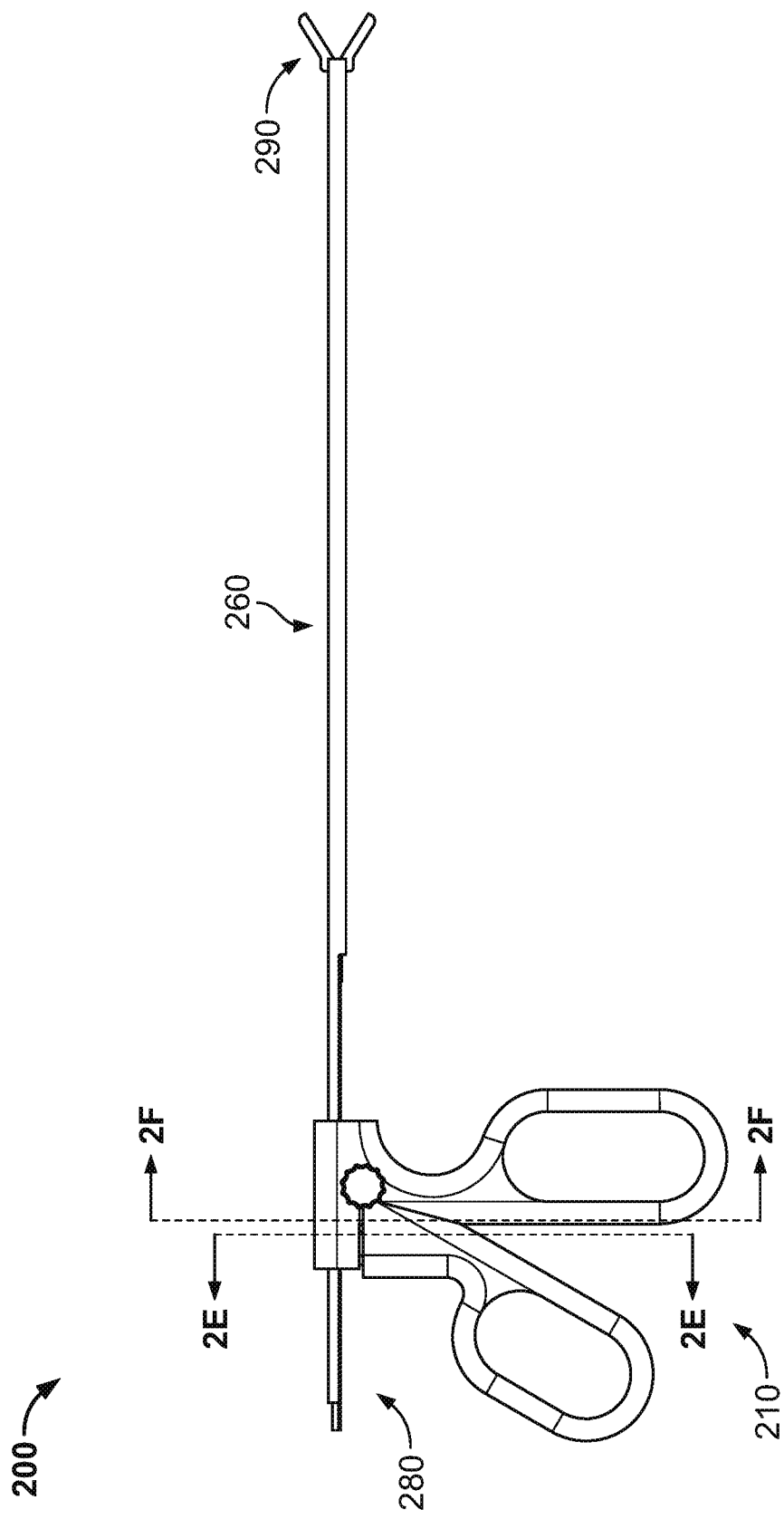

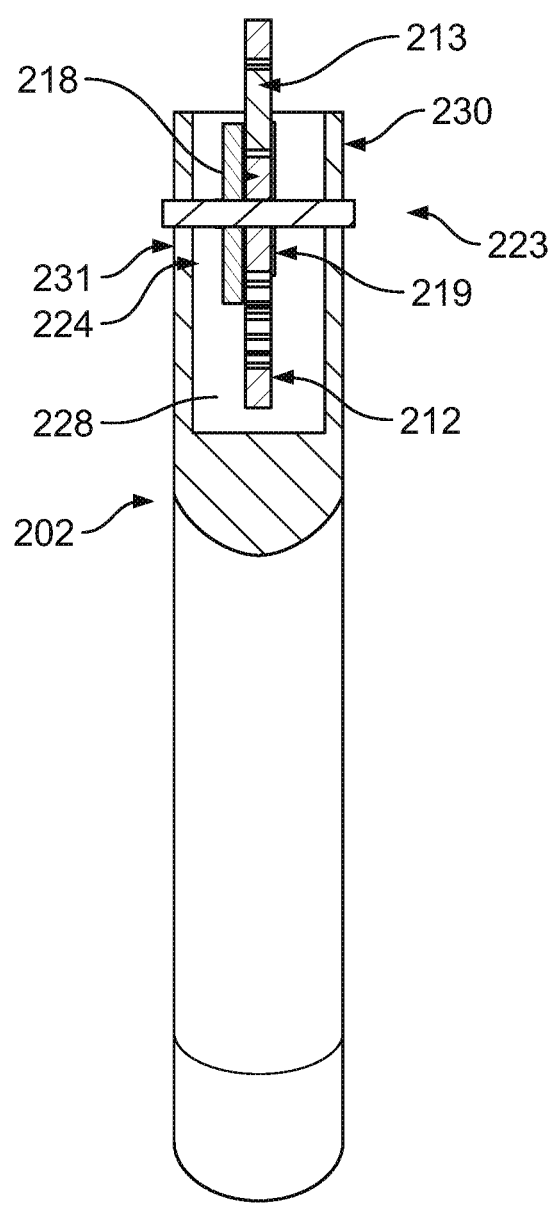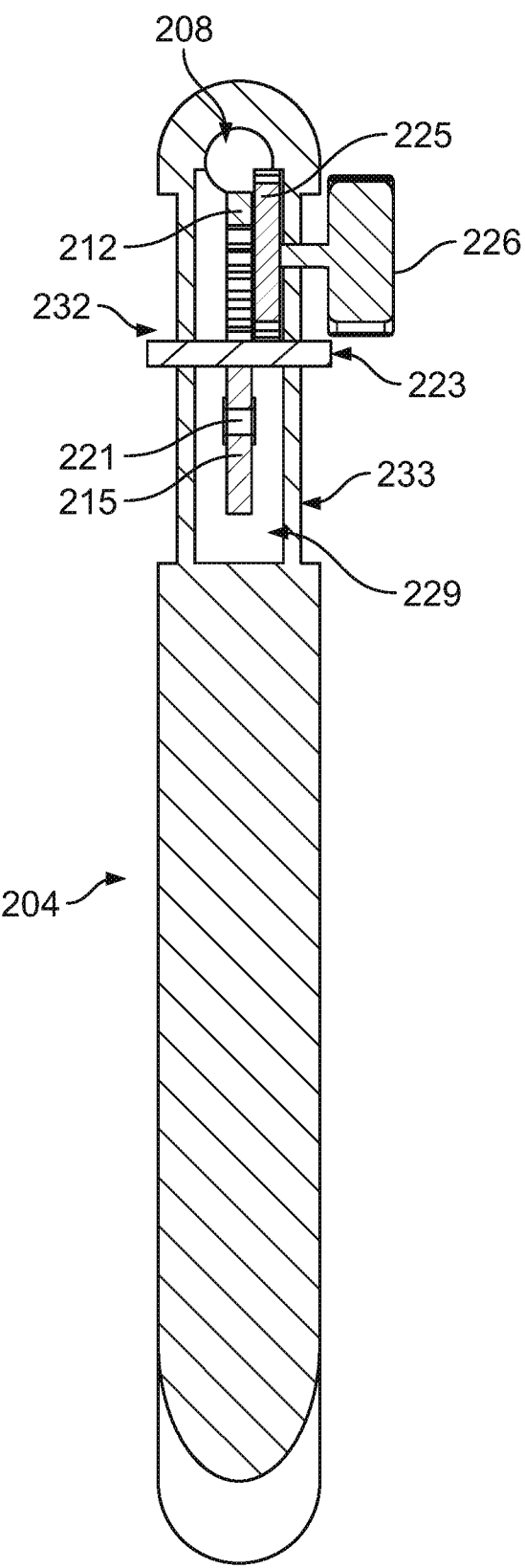
FIG. 2E
FIG. 2F

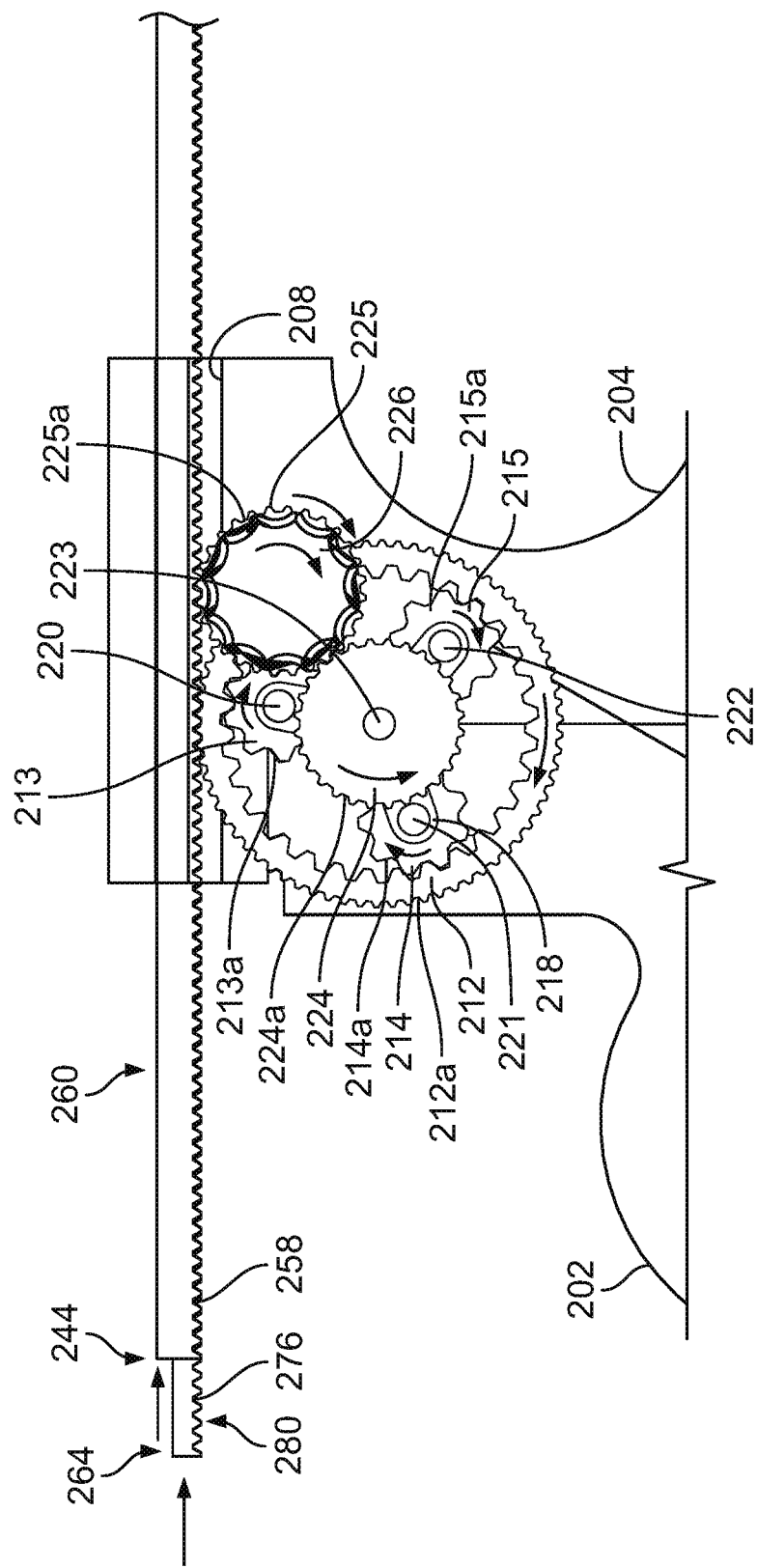

ADJUSTABLE LENGTH LAPAROSCOPIC INSTRUMENT

TECHNICAL FIELD

The present disclosure relates generally to medical devices, and more particularly to adjustable length laparoscopic instruments.

BACKGROUND

As depicted in FIG. 1, a typical monopolar electrosurgical laparoscopic instrument 100 generally has five main components: a handle 102, an outer shaft 104 extending longitudinally from the handle, an actuation rod 106 extending through the outer shaft, an electrode 108 in electroconductive contact with the actuation rod 106, and an actuatable end effector 110, disposed at the distal end of the device. The handle 102 illustrated is a "ring handle", which has a stationary finger portion 112 attached to the outer shaft 104, and an actuatable thumb portion 114 attached to the actuation rod 106. Actuation of the thumb portion 114 by pivoting relative to the finger portion 112 moves the actuation rod 106 longitudinally within the outer shaft 104 to operate the end effector 110. Operating an end effector may cause the end effector to perform various tissue manipulating functions. For example, end effector 110 is depicted as having two opposed jaws, and operating end effector 110 may cause the two opposed jaws to open and close, for example to grasp or dissect tissue.

Although many different variations of each of the above components have been introduced into the art, there exists a need for designs that provide surgeons and other users with ergonomic features to enhance safety and ease of use.

BRIEF SUMMARY

Typically, laparoscopic instruments come with a set shaft length, for example 24 cm, or 36 cm, or 45 cm. Laparoscopic instruments with set shaft lengths present various problems in performing procedures. For example, throughout the course of a procedure, a user may need to manipulate tissue at various locations within the patient. To do so using a single access port, the user may need to insert the instrument's distal end further into the patient, or withdraw the instrument's distal end back towards the user, in manners that are not ergonomic. Longer set shaft lengths for laparoscopic instruments have been implemented as the patient population becomes larger (e.g. bariatric), because for larger patients the distance between the trocar and the intended site of tissue manipulation is longer. These longer set shaft lengths can particularly exacerbate the above-mentioned ergonomic problems. For example, if a substantial portion of the shaft needs to be withdrawn towards the user, the user's hands may be far from the patient, making it difficult to operate the instrument or related visualization equipment. Another option to manipulate tissue at various locations within the patient is to use multiple access ports, but this causes additional scarring and trauma to the patient. A third option is to switch to a different set shaft length instrument during the procedure, but this extends operating time and complicates the procedure.

Set shaft lengths present administrative problems as well, because a hospital needs to stock and keep track of the different set shaft lengths. For example, set shaft lengths necessitate individual stock keeping units (SKUs) for each different set shaft length, which can increase hospital administrative costs. Further, set shaft lengths can increase hospital overhead costs by increasing required storage space.

Accordingly, a need exists for adjustable length laparoscopic instruments. Aspects and embodiments of the present disclosure are configured to address that need, and in doing so they may address one or more of the above problems and provide various benefits. Aspects and embodiments of the present disclosure may provide laparoscopic instruments that are more ergonomic than existing laparoscopic instruments, for example by allowing the user to choose a more comfortable shaft length for a given procedure or step of a procedure. Aspects and embodiments of the present disclosure may reduce or eliminate the need for multiple SKUs for different set shaft lengths. Aspects and embodiments of the present disclosure may reduce the number of access ports needed to reach tissue at various locations within the patient, and may thus reduce scarring and trauma to the patient. Aspects and embodiments of the present disclosure may reduce operating time and complexity by reducing the necessary number of instrument changes. Those of skill in the art having the benefit of the present disclosure may recognize that aspects and embodiments of the present disclosure solve additional problems and provide additional benefits, both in laparoscopic instruments and in other tools with end effectors. For example, those of skill in the art will appreciate that aspects and embodiments of the present disclosure, for example the discussed length adjustment mechanisms, may be used with a variety of tools with end effectors (e.g., needle holders, clamps, scissors, dissectors, graspers, etc.), and that such uses may be practiced within the scope of the present disclosure.

In one aspect of the present disclosure, a laparoscopic instrument is provided. The instrument includes a shaft with a shaft distal end and a shaft proximal end. The instrument further includes an actuation rod with an actuation rode distal end and an actuation rod proximal end. The actuation rod is receivable by the shaft such that the actuation rod can translate longitudinally relative to the shaft to actuate an end effector. The instrument further includes a handle configured to hold the shaft and the actuation rod. The handle is configured to cause the actuation rod to translate longitudinally relative to the shaft to actuate the end effector. The instrument further includes a length adjustment mechanism configured to adjust a shaft length. The shaft length is defined between the handle and the shaft distal end.

BRIEF DESCRIPTION OF THE DRAWINGS

FIG. 2 shows an assembled view of a first embodiment of a laparoscopic instrument;

FIG. 2E shows a transverse section view of a thumb ring member of the handle and the gear mechanism taken along line 2E-2E of FIG. 2;

FIG. 2F shows a transverse section view of a finger ring member of the handle and a gear mechanism taken along line 2F-2F of FIG. 2;

FIGS. 2P and 2Q show partial views of a proximal portion of the laparoscopic instrument of FIG. 2, with arrows indicating motion of various components during operation in a length adjustment configuration, and the handle shown in outline;

DETAILED DESCRIPTION

Figure 1:
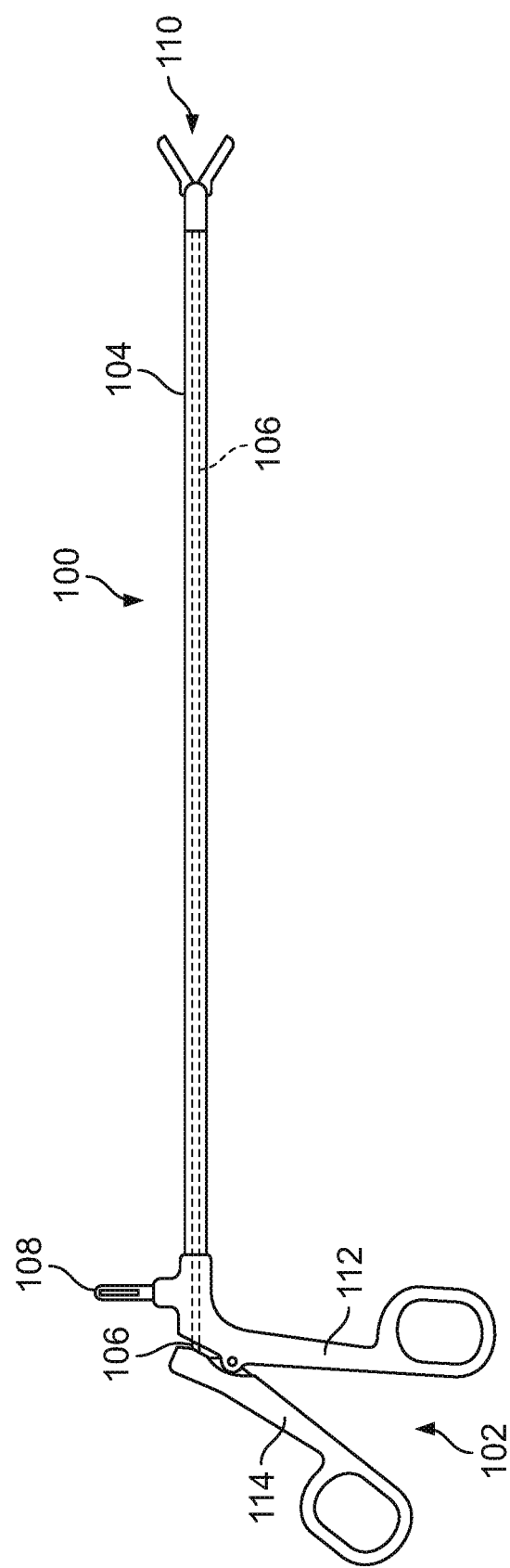
FIG. 1 shows a prior art laparoscopic instrument.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

Overview of Laparoscopic Instrument 200

Figure 2A:
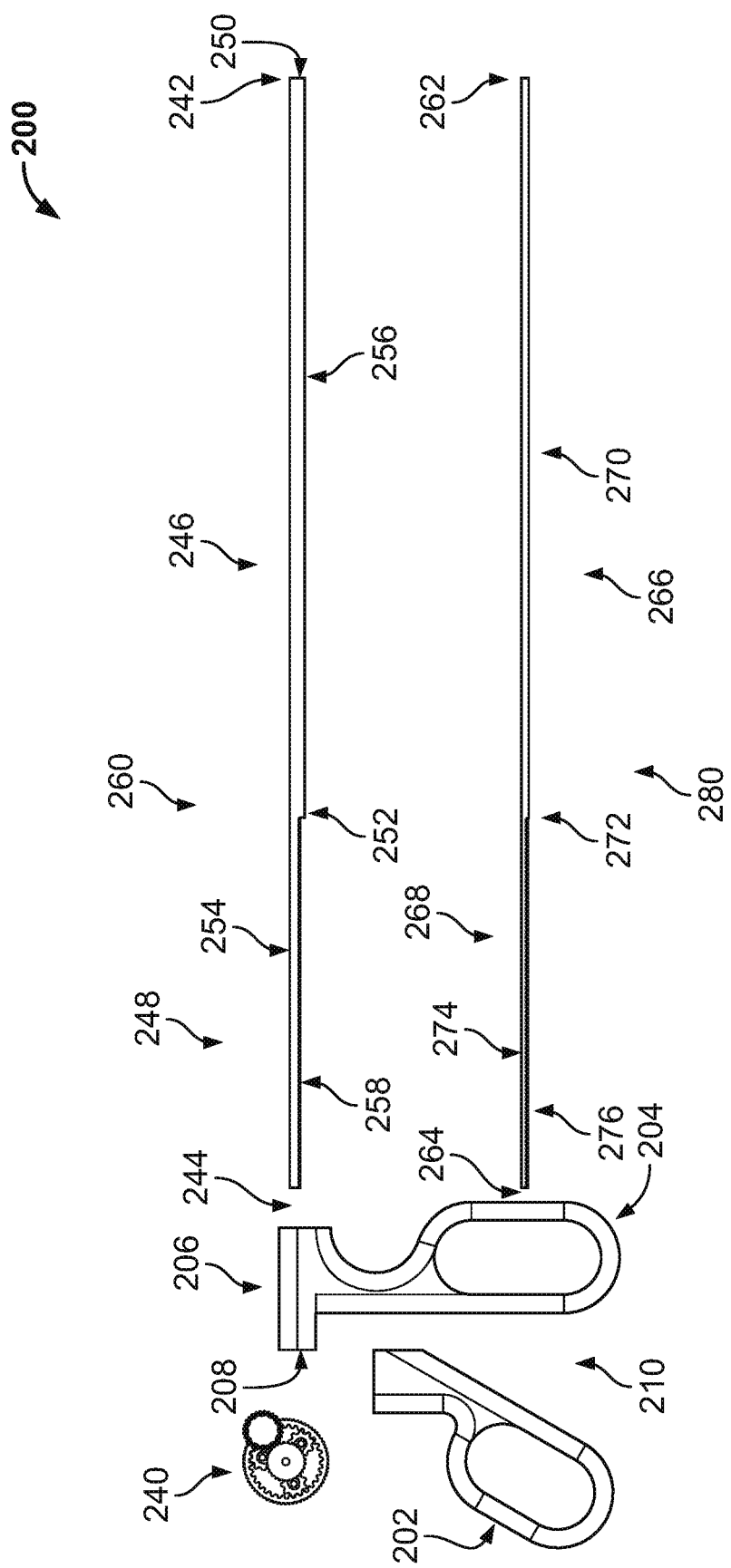
FIG. 2A shows a partially disassembled view of the laparoscopic instrument of FIG. 2.
Figure 2B:
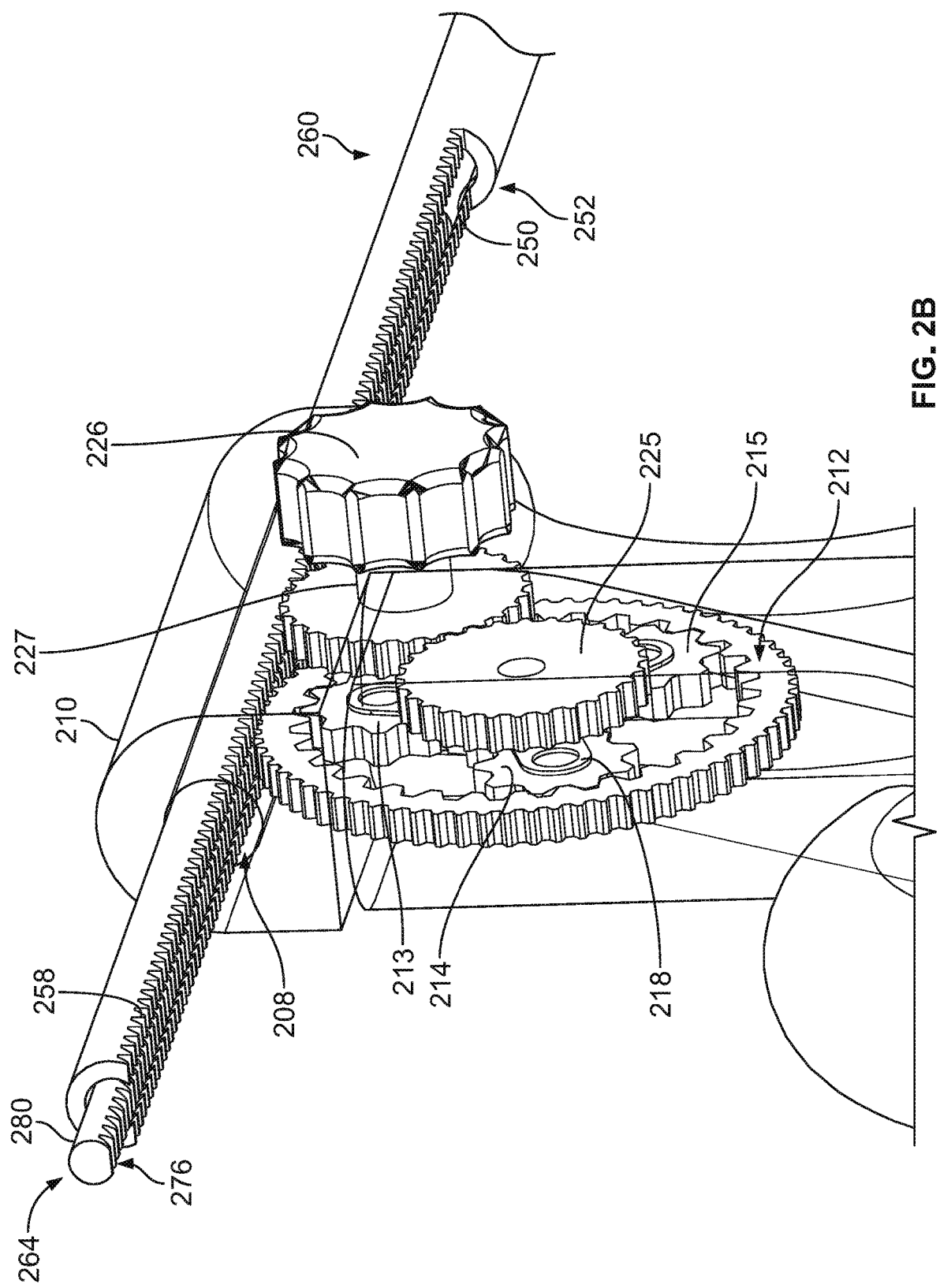
FIG. 2B shows a partial perspective view of a proximal portion of the laparoscopic instrument of FIG. 2, with a handle shown in outline to reveal internal details.

The exterior of a laparoscopic instrument 200 is illustrated with reference to FIG. 2. Laparoscopic instrument 200 is an adjustable length laparoscopic instrument. FIG. 2A is a partially disassembled view of laparoscopic instrument 200, and shows that laparoscopic instrument 200 includes a handle 210, a gear mechanism 240, a shaft 260, and an actuation rod 280. As shown in FIG. 2, but omitted in FIGS. 2A-2Q for clarity, an end effector 290 may be disposed at a distal end of laparoscopic instrument 200 and operably connected to shaft 260 and actuation rod 280 in a manner known to those skilled in the art. FIG. 2B is a partial perspective view of a proximal end of laparoscopic instrument 200 with handle 210 depicted in outline for clarity.

Handle 210 includes a thumb ring member 202 (commonly referred to as a "thumb bow") pivotably attached to a finger ring member 204 (commonly referred to as a "finger bow") in a manner described in further detail below. Handle 210 also includes a shaft holder 206 fixedly connected to the top of finger ring member 204. Shaft holder 206 defines a lumen 208 extending through its length and open at distal and proximal ends of shaft holder 206. Lumen 208 is configured to receive and hold a portion of shaft 260 such that shaft 260 can longitudinally translate therein.

Shaft 260 extends from shaft distal end 242 to shaft proximal end 244 and includes a shaft distal section 246 and an adjacent shaft proximal section 248. Shaft distal section 246 includes a substantially tubular wall 256 defining a lumen 250. Lumen 250 extends through the length of shaft distal section 246 and is open at shaft distal end 242 and at intermediate point 252. Lumen 250 is configured to receive and hold actuation rod 280 such that actuation rod 280 can longitudinally translate therein with respect to shaft 260. At intermediate point 252, a lower portion of substantially tubular wall 256 terminates, but a top portion of substantially tubular wall 256 continues to extend proximally until terminating at shaft proximal end 244, thus defining arcuate wall 254 of shaft proximal section 248. Shaft teeth 258 of shaft proximal section 248 extend along both bottom facing longitudinal edges of arcuate wall 254 from shaft proximal end 244 to intermediate point 252.

Actuation rod 280 extends from actuation rod distal end 262 to actuation rod proximal end 264 and includes an actuation rod distal section 266 and an actuation rod proximal section 268. Actuation rod distal section 266 includes a substantially cylindrical rod 270 extending from actuation rod distal end 262 to intermediate point 272. At intermediate point 272, actuation rod teeth 276 of actuation rod proximal section 268 begin. Actuation rod teeth 276 extend along at least a bottom portion of actuation rod proximal section 268 from intermediate point 272 to actuation rod proximal end 264.

In some embodiments, actuation rod teeth 276 may extend around the full circumference of actuation rod proximal section 268. This configuration may provide an additional benefit in that if the end effector 290 is coupled to shaft 260 with a swivel at any point distal to actuation rod distal section 266, the end effector 290 could be rotated about the longitudinal axis of shaft 260 to a desired orientation, for example by coupling a rotation knob to actuation rod proximal end 264 and rotating it.

Arcuate wall 254 does not define a full tubular wall. Accordingly, when actuation rod 280 is received within shaft 260, a portion of actuation rod 280 longitudinally coextensive with shaft proximal section 248 is downwardly exposed such that transverse contact can be made with that portion of actuation rod 280 from below. For example, as illustrated in FIG. 2B, when actuation rod 280 is received within shaft 260, and both are thus received in shaft holder 206, portions of gear mechanism 240 that extend upward into lumen 208 are able to engage both with actuation rod teeth 276 and with shaft teeth 258 that are located on one of the bottom facing longitudinal edges of arcuate wall 254. Those engagements are described further below in connection with a description of gear mechanism 240. Moreover, shaft 260 and actuation rod 280 are not connected to the handle at a fixed point, but pass through handle 210 and extend out the back, which enables adjustment of both a length of shaft 260 that extends distally from handle 210 and a length of actuation rod 280 that extends distally from handle 210.

Components of gear mechanism 240, along with shaft teeth 258 and/or actuation rod teeth 276, can act together as a length adjustment mechanism of laparoscopic instrument 200. Additionally, components of gear mechanism 240, along with handle 210 and actuation rod teeth 276, can act together to cause actuation rod 280 to translate longitudinally relative to shaft 260 to actuate the end effector 290.

Figure 2C:
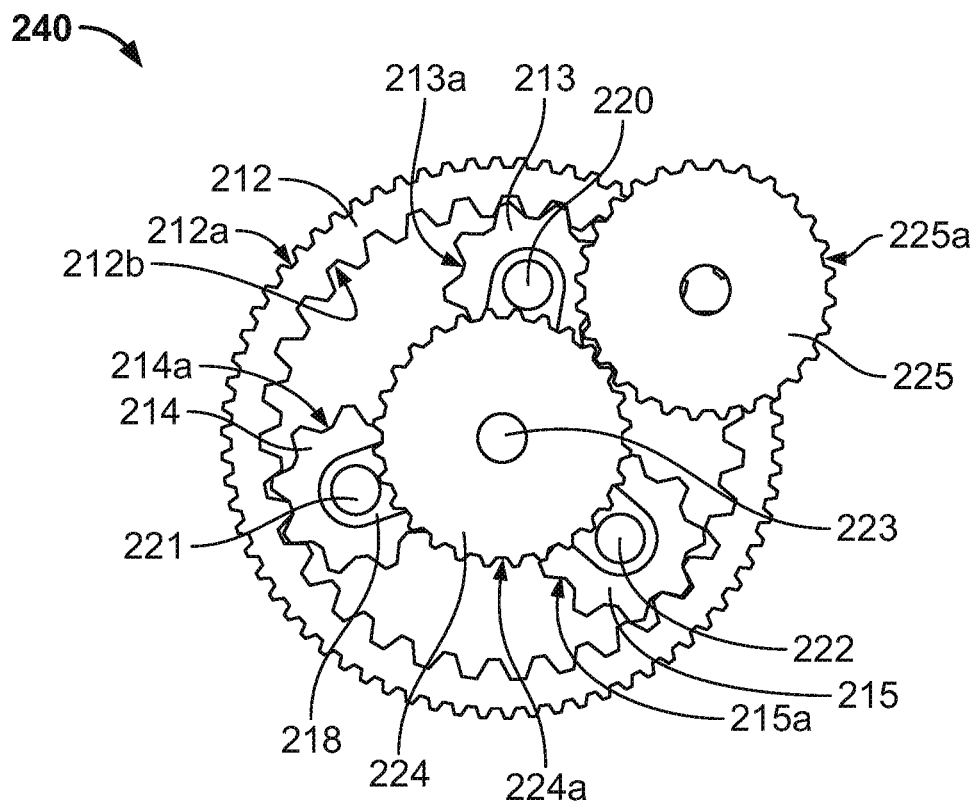
FIG. 2C shows an isolated side view of a gear mechanism of the laparoscopic instrument of FIG. 2.
Figure 2D:
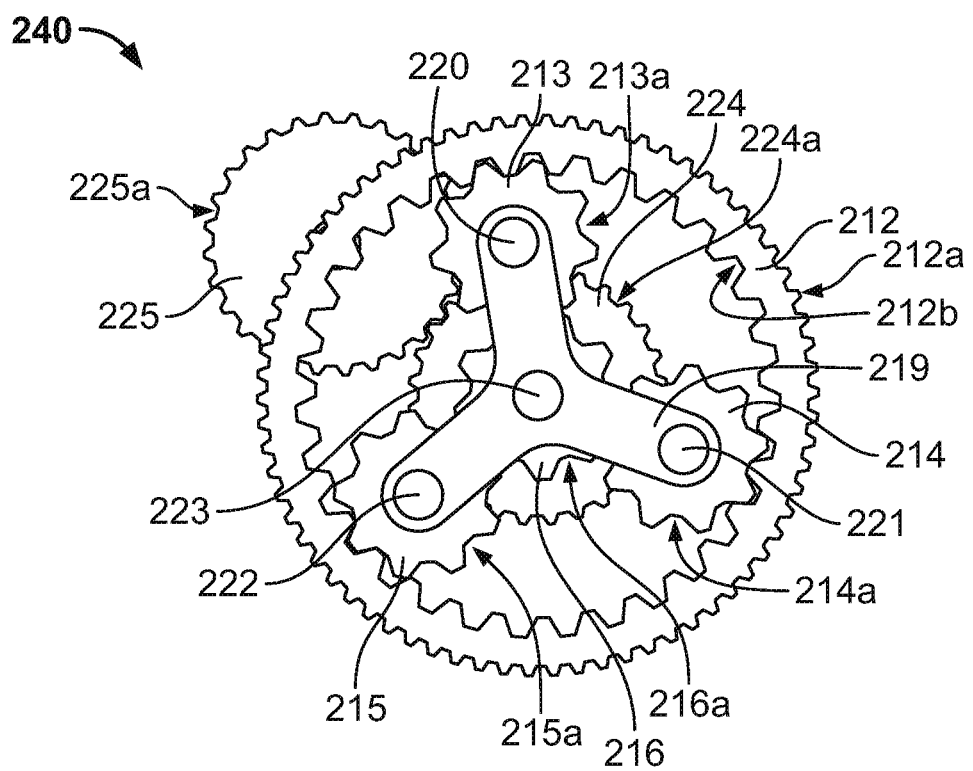
FIG. 2D shows an isolated opposite side view of the gear mechanism of the laparoscopic instrument of FIG. 2.

FIG. 2C is an isolated side view of gear mechanism 240 with the other components of laparoscopic instrument 200 omitted for clarity. FIG. 2E is an opposite isolated side view of gear mechanism 240 with the other components of laparoscopic instrument 200 omitted for clarity. Gear mechanism 240 includes a planetary gear mechanism that includes a ring gear 212, three planet gears 213, 214, 215, a sun gear 216, and two Y-brackets 218, 219. Ring gear 212 is generally ring shaped and includes outer teeth 212a surrounding its outer circumferential surface and inner teeth 212b surrounding its inner circumferential surface. Ring gear outer teeth 212a are sized and spaced to be engagingly complementary to actuation rod teeth 276. Planet gears 213, 214, 215 are configured to be received within ring gear 212 symmetrically surrounding sun gear 216. Planet gears 213, 214, 215 each include respective outer teeth 213a, 214a, 215a, surrounding their respective outer circumferential surfaces. Planet gear outer teeth 213a, 214a, 215a are sized and spaced to be engagingly complementary to both ring gear inner teeth 212b and sun gear outer teeth 216a. Planet gears 213, 214, 215, are held in position symmetrically surrounding sun gear 216 by being sandwiched between Y-brackets 218, 219. Pins 220, 221, 222 extend between and join Y-brackets 218, 219 and serve as rotational bearings upon which planet gears 213, 214, 215 are mounted and about which they can rotate.

A bearing shaft 223 extends through respective bearing holes in the respective centers of sun gear 216 and Y-brackets 218, 219, about which they can rotate in certain configurations, as described later in more detail. Sun gear 216 may be rigidly coupled to shaft gear 224. Shaft gear 224 also includes a bearing hole in its respective center through which bearing shaft 223 extends. Shaft gear 224 can rotate about bearing shaft 223 in certain configurations. Rotation of sun gear 216 about bearing shaft 223 causes rotation of shaft gear 224 about bearing shaft 223. The coupling of sun gear 216 and shaft gear 224 may be through a connecting hub extending coaxially over bearing shaft 223 from sun gear 216 to shaft gear 224. The connecting hub may be mounted over bearing shaft 223 such that the connecting hub can rotate about bearing shaft 223 along with sun gear 216 and shaft gear 224. In embodiments including such a connecting hub, the respective center holes of Y-brackets 218, 219 may be mounted on and capable of rotating about the connecting hub, rather than directly on bearing shaft 223. This may allow Y-brackets 218, 219 to rotate about the axis of bearing shaft 223 in unison with each other but independent of sun gear 216 and shaft gear 224.

Gear mechanism 240 also includes a knob gear 225 offset radially from bearing shaft 223 and including outer teeth 225a. Knob gear outer teeth 225a are sized and spaced to be engagingly complementary to both shaft gear outer teeth 224a and shaft teeth 258. Gear mechanism 240 may also include a control knob 226 coupled to knob gear 225. Control knob 226 may be configured to, when rotated by a user, in at least some configurations, cause knob gear 225 to rotate in a corresponding manner about a corresponding axis of rotation radially offset from bearing shaft 223. For example, as depicted in FIG. 2B control knob 226 may be rigidly connected to knob gear 225 by knob shaft 227.

Gear mechanism 240 is mounted to handle 210. FIG. 2E is a front sectional view of thumb ring member 202 and gear mechanism 240 taken at line 2E-2E of FIG. 2, with the other components of laparoscopic instrument 200 omitted for clarity. As depicted in FIG. 2E, thumb ring member 202 defines an internal cavity 228 configured to receive portions of gear mechanism 240, and portions of finger ring member 204, when thumb ring member 202 and finger ring member 204 are coupled to each other. One or both of Y-brackets 218, 219 are coupled to thumb ring member 202, for example within internal cavity 228. Bearing shaft 223 extends across internal cavity 228 and is coupled to walls 230, 231 such that bearing shaft 223 can rotate about its axis and relative to thumb ring member 202.

FIG. 2F is a rear sectional view of finger ring member 204 and gear mechanism 240 taken at line 2F-2F of FIG. 2, with the other components of laparoscopic instrument 200 omitted for clarity. As depicted in FIG. F, finger ring member 204 defines an internal cavity 229 configured to receive portions of gear mechanism 240. Internal cavity 229 extends upwards into shaft holder 206, and is continuous with lumen 208, such that knob gear 225 and ring gear 212 are able engage with shaft 260 and actuation rod 280 when they are received in lumen 208.

When handle 210 is assembled, bearing shaft 223 extends through bearing holes in walls 232, 233 of finger ring member 204, and rotatably couples to walls 230, 231 of thumb ring member 202 as discussed above, such that bearing shaft 223 can rotate about its axis and relative to both thumb ring member 202 and finger ring member 204. Bearing shaft 223 thus acts to pivotably connect thumb ring member 202 with finger ring member 204. Handle 210 may further include a mechanism to selectively prevent rotation of sun gear 216 and shaft gear 224 relative to thumb ring member 202. Such a mechanism may, for example, include a slide switch which when slid in a first direction jams knob gear 225 and/or control knob 226, such that one or both of them cannot freely rotate, and which, when slid in a second direction, allows knob gear 225 and/or control know 226 to rotate freely.

As will become apparent, this mechanism may also act to prevent unintended length adjustment by the user. In some embodiments, rather than jamming knob gear 225 and/or control knob 226, the slide switch could mechanically interfere with some other gear of gear mechanism 240, shaft 260, or other moving elements of laparoscopic instrument 200. For embodiments that mechanically interfere with shaft 260, the switch could be shaped as a button, which may have a spring-driven return, so pressing the button unlocks the mechanism and releasing the button restores the jamming element to a locking position. Or, a series of teeth or slots could be included on a top surface of shaft proximal section 248, an opening could be included through a top surface of shaft holder 206, and a tooth could be coupled to shaft holder 206 that could slide or rotate through the opening to engage the teeth or slots in the top surface of shaft proximal section 248.

Alternative or additional mechanisms for preventing unintended length adjustment by the user could be implemented. For example, friction between rotating components (e.g. control knob 226, gears of gear mechanism 240, and/or shafts) and stationary parts of handle 210 may provide this feature. The friction would need to be sufficient to prevent unintentional movement of shaft 260 and actuation rod 280, but easily overcome by the user when desired. One way to enhance the use of friction may be to link control knob 226 to knob gear 225 with an additional gear. For example, instead of configuring control knob 226 concentrically on the same knob shaft 227 as knob gear 225, control knob 226 and an attached small spur gear may be positioned in an offset location (e.g. 1 cm toward the distal end of laparoscopic instrument 200) such that the small spur gear meshes with knob gear 225. A gear ratio between knob gear 225 and the small spur gear would be such that it is very easy to overcome friction and adjust shaft length when intended, but very difficult for forces exerted on shaft 260 to back-drive gear mechanism 240 to turn control knob 226.

In another exemplary mechanism for preventing unintended length adjustment, a detent or similar arrangement that creates spatially irregular resistance may be included. For example, laparoscopic instrument 200 could include pointed or spherical features forced elastically against a radial or longitudinal surface of control knob 226, a gear of gear mechanism 240, or some other part of laparoscopic instrument 200. The surface could include a series of indents, so the mechanism is biased to rest with the pointed or spherical feature in an indent. This mechanism would briefly require additional force/torque to move past each detent, which is more likely to happen as a result of a user's intended movement, but would require less exertion than other friction-based mechanisms because the friction would be reduced when the pointed or spherical features are between indents.

Another exemplary mechanism for preventing unintended length adjustment may include a toothed or crenelated face of control knob 226, and a corresponding toothed or crenelated face on handle 210. When such a control knob 226 is close to handle 210, the features of the faces would interdigitate to lock rotation of control knob 226. Such a control knob 226 could slide along its axis of rotation, with knob shaft 227 being appropriately keyed/splined to maintain rotational alignment of control knob 226 and knob gear 225. When control knob 226 is slid out, away from the body, the locking features are separated and control knob 226 can be rotated freely. In some embodiments, control knob 226 could be configured to automatically return to the locked position when released, for example via a spring or similar element that would pull control knob 226 back towards handle 210.

Operation of Laparoscopic Instrument 200

When laparoscopic instrument 200 is fully assembled consistent with the above description, it can be set in an end effector actuation configuration so that it can be operated by the user to actuate an end effector 290. It can also be set in a length adjustment configuration so that it can be operated by the user to adjust a shaft length defined between the handle 210 and the shaft distal end.

End Effector Actuation Configuration

Figure 2G:
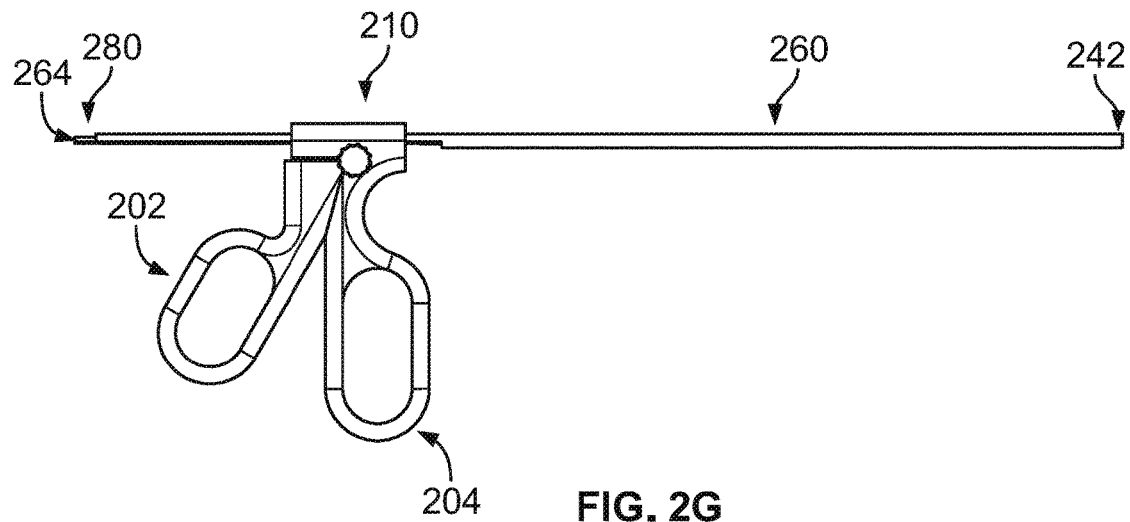
FIGS. 2G-2I show various positions of the laparoscopic instrument of FIG. 2 during end effector actuation.
Figure 2H:
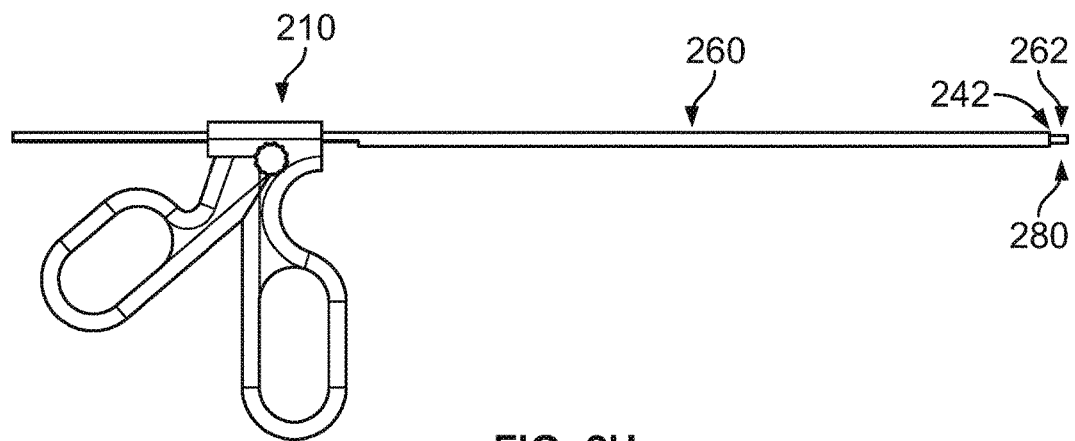
Figure 2I:
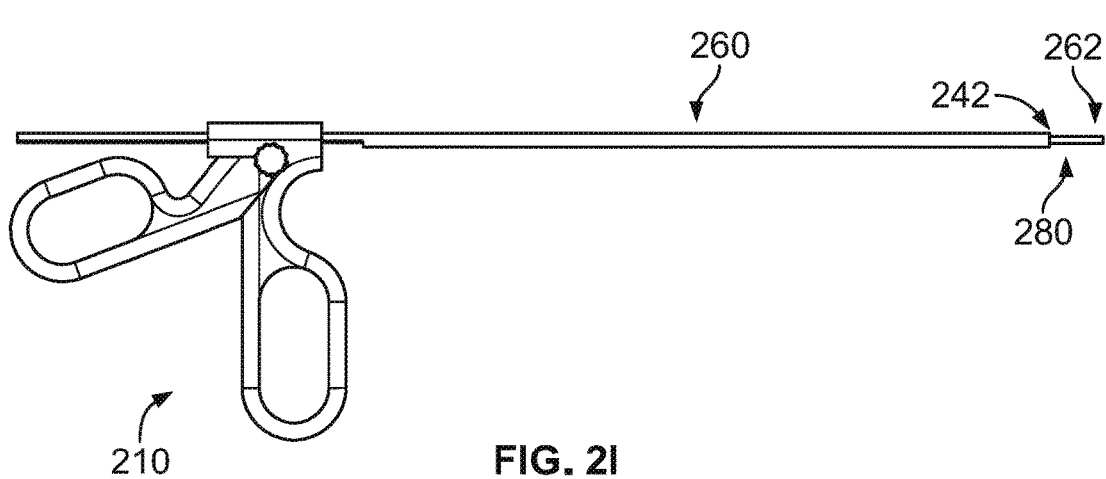

Operation of laparoscopic instrument 200 in an end effector configuration is described with reference to FIGS. 2G-2K. FIGS. 2G-2I are exterior views of laparoscopic instrument 200 with end effector 290 removed for clarity. In the end effector actuation configuration, as seen for example in a progression from FIG. 2G to 2I, generally, when thumb ring member 202 is pivoted away from finger ring member 204, actuation rod 280 is caused to translate longitudinally in a direction away from handle 210. As shown, the more thumb ring member 202 pivots away from finger ring member 204, the farther actuation rod distal end 262 is positioned from handle 210. Similarly, as shown in a progression from FIGS. 2I to 2G, when thumb ring member 202 is pivoted towards finger ring member 204, actuation rod 280 is caused to translate longitudinally in a direction away from handle 210. The more thumb ring member 202 pivots towards finger ring member 204, the closer actuation rod distal end 262 is positioned to handle 210.

Figure 2J:
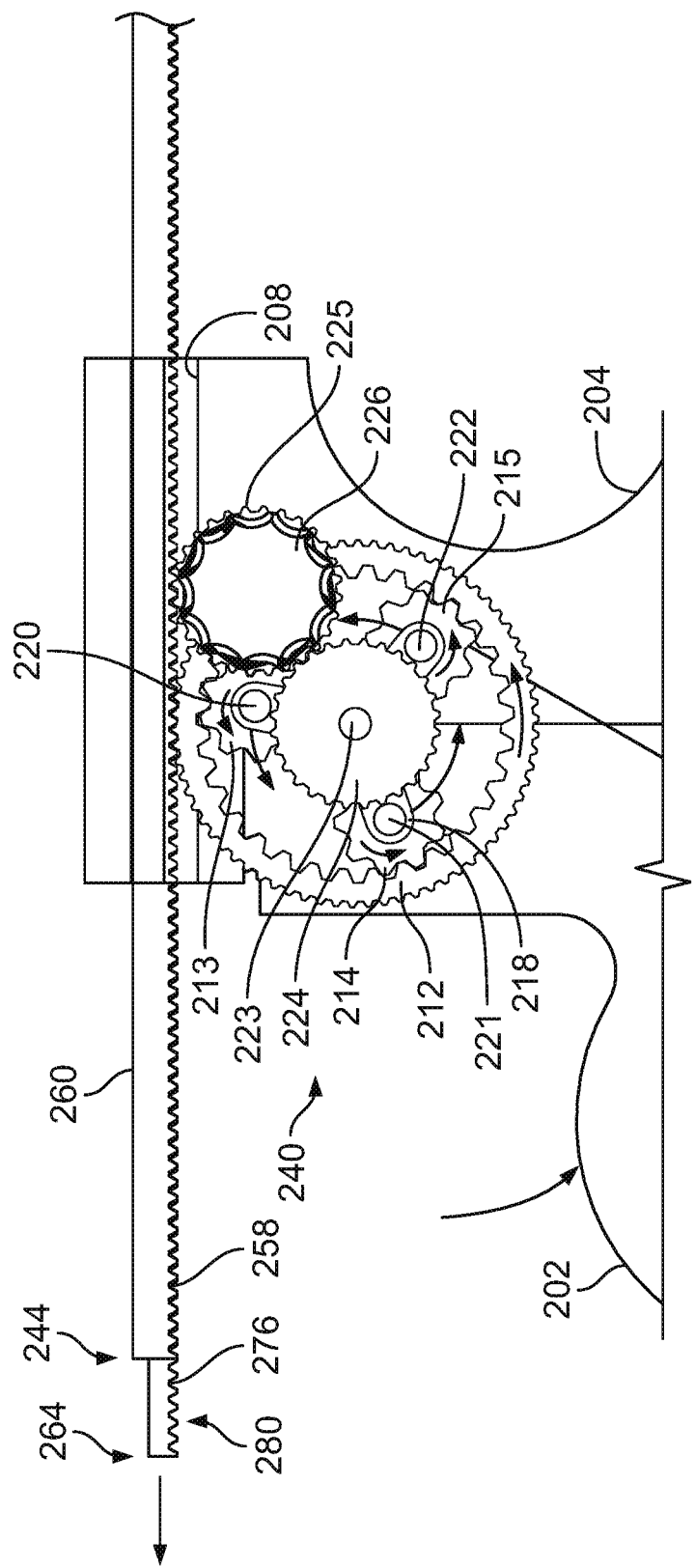
FIGS. 2J and 2K show partial views of a proximal portion of the laparoscopic instrument of FIG. 2, with arrows indicating motion of various components during operation in an end effector actuation configuration, and the handle shown in outline.
Figure 2K:
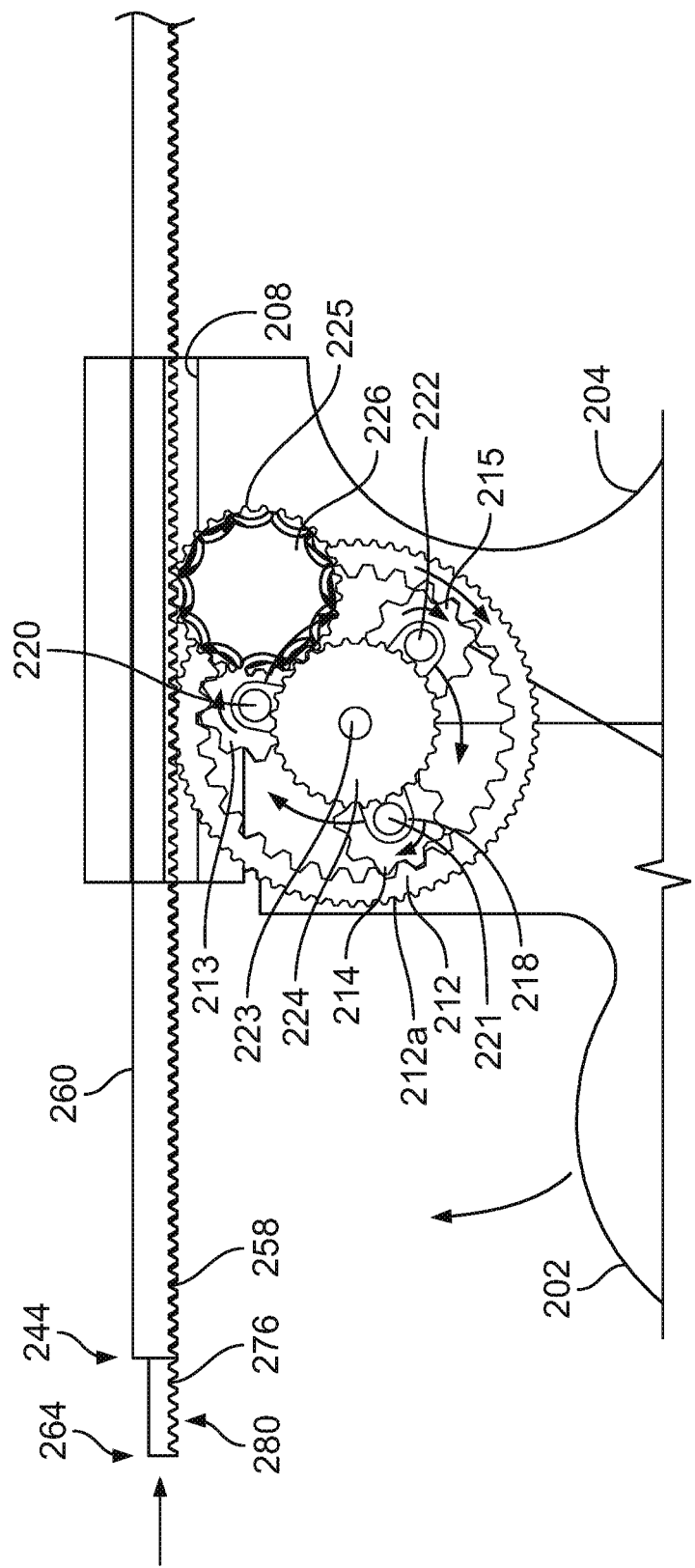

FIGS. 2J and 2K are partial views of a proximal portion of laparoscopic instrument 200, with arrows indicating motion of various components during operation in the end effector actuation configuration, and handle 210 shown in outline for clarity. In the end effector actuation configuration, the mechanism to selectively prevent rotation of sun gear 216 and shaft gear 224 relative to thumb ring member 202 may be engaged. Sun gear 216 and shaft gear 224 may however rotate about bearing shaft 223 so as to remain rotationally fixed with respect to thumb ring member 202, which motion is not shown in FIGS. 2J and 2K.

In the end effector actuation configuration, due to the nature of the described planetary gear mechanism, and, as shown in FIG. 2J, when the thumb ring member 202 is pivoted towards finger ring member 204, planet gears 213, 214, 215 are caused to rotate in a counter-clockwise manner about pins 220, 221, and 222 and to walk along ring gear inner teeth 212b. Y-brackets 218, 219 are caused to rotate about bearing shaft 223 in a counter-clockwise manner. Ring gear 212 is caused to rotate about bearing shaft 223 in a counter-clockwise manner. Because ring gear outer teeth 212a engage with actuation rod teeth 276, and actuation rod 280 is able to translate longitudinally relative to shaft 260, this rotation of ring gear 212 causes actuation rod 280 to translate longitudinally such that actuation rod distal end 262 moves closer to handle 210 and actuation rod proximal end 264 moves farther from handle 210. However, pivoting thumb ring member 202 relative to finger ring member 204 does not cause shaft 260 to translate longitudinally relative to handle 210.

Similarly, as shown in FIG. 2K, when thumb ring member 202 is pivoted away from finger ring member 204, planet gears 213, 214, 215 are caused to rotate in a clockwise manner about pins 220, 221, and 222 and to walk along ring gear inner teeth 212b. Y-brackets 218, 219 are caused to rotate about bearing shaft 223 in a clockwise manner. Ring gear 212 is caused to rotate about bearing shaft 223 in a clockwise manner. Because ring gear outer teeth 212a engage with actuation rod teeth 276, and actuation rod 280 is able to translate longitudinally relative to shaft 260, this rotation of ring gear 212 causes actuation rod 280 to translate longitudinally such that actuation rod distal end 262 moves farther from handle 210 and actuation rod proximal end 264 moves closer to handle 210. However, pivoting thumb ring member 202 relative to finger ring member 204 does not cause shaft 260 to translate longitudinally relative to handle 210.

As is recognized by those skilled in the art, the longitudinal translation of actuation rod 280 relative to handle 210 and shaft 260 that is produced by operating laparoscopic instrument 200 in the end effector actuation configuration can be used to operate an end effector 290 coupled at the distal end of laparoscopic instrument 200 in a variety of manners.

Length Adjustment Configuration

Figure 2L:
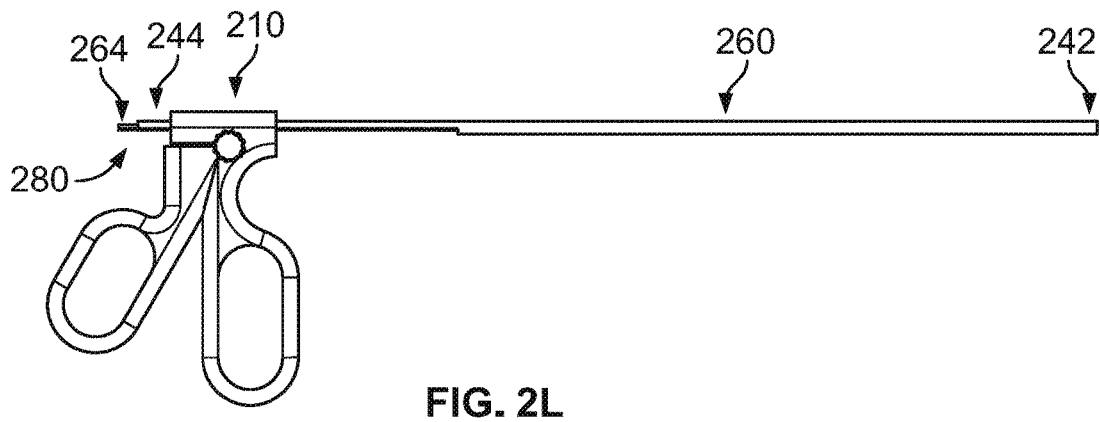
FIGS. 2L-2N show various positions of the laparoscopic instrument of FIG. 2 during length adjustment operations.
Figure 2M:
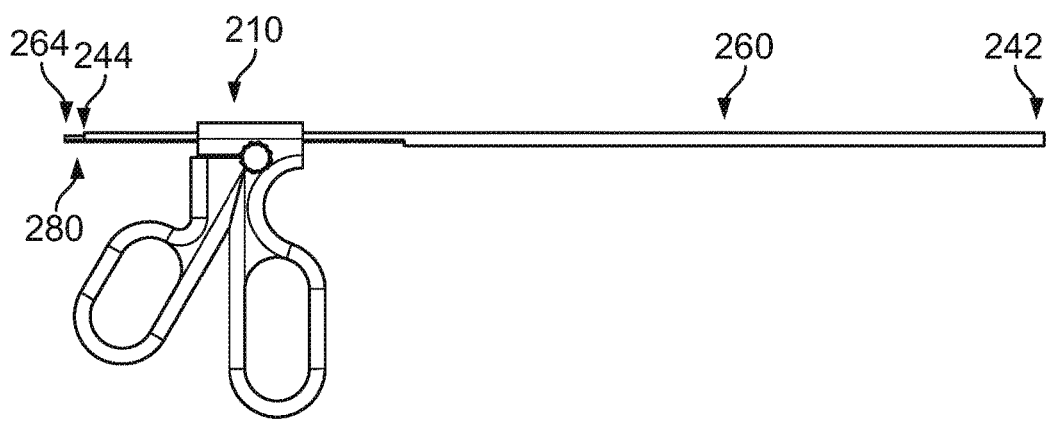
Figure 2N:
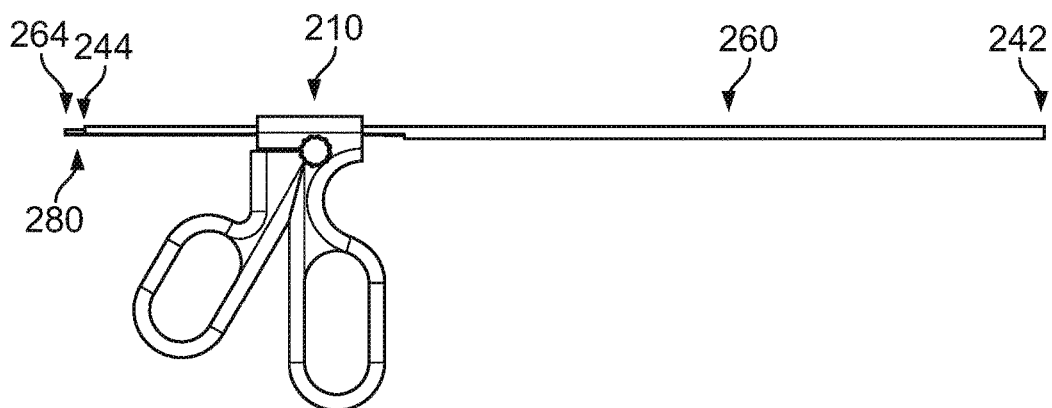
Figure 2P:
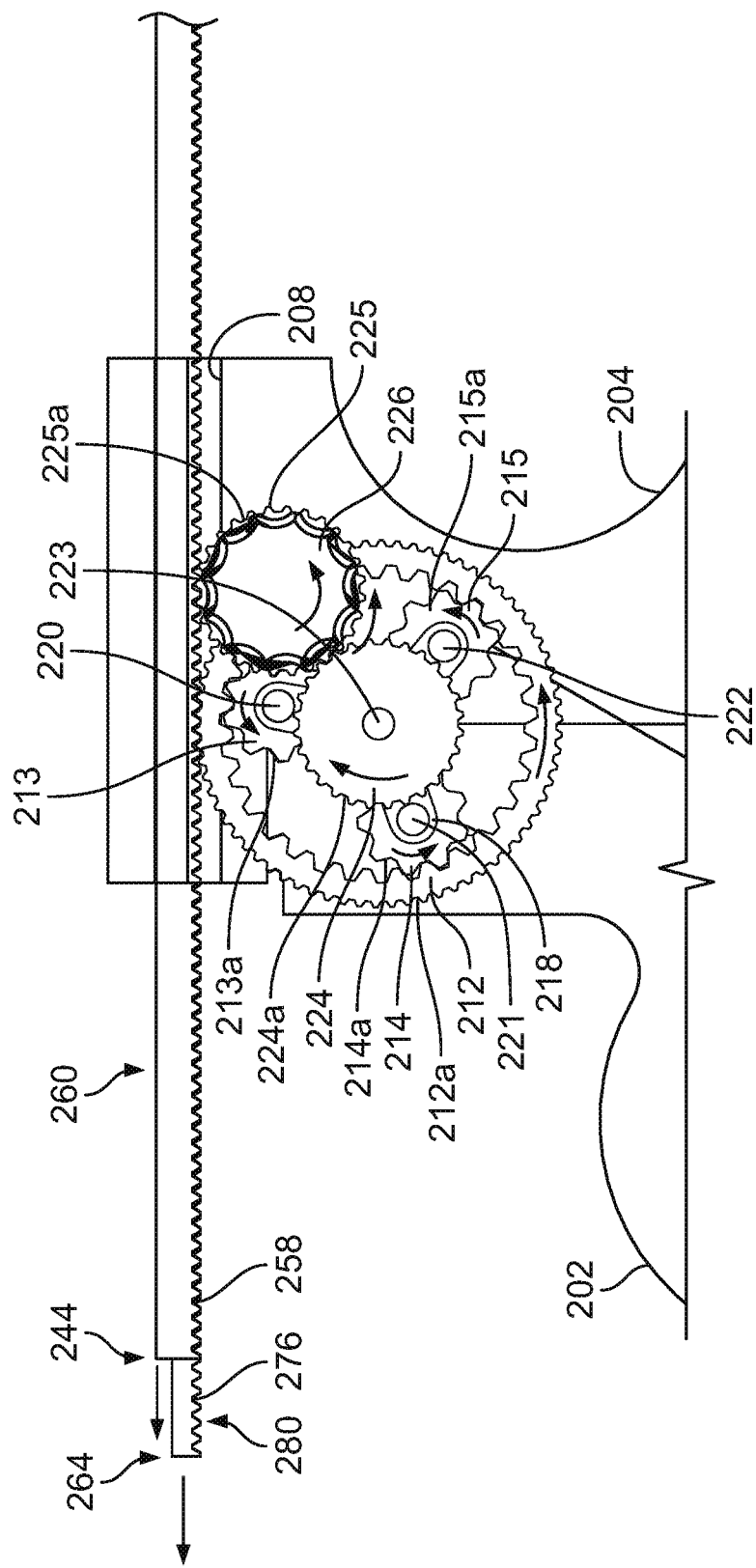

Operation of laparoscopic instrument 200 in a length adjustment configuration is described in connection with FIGS. 2L-2Q. FIGS. 2L-2N are exterior views of laparoscopic instrument 200 with end effector 290 removed for clarity. FIGS. 2P and 2Q are partial views of a proximal portion of laparoscopic instrument 200, with arrows indicating motion of various components during operation in the length adjustment configuration, and handle 210 shown in outline for clarity. In the length adjustment configuration, generally, when knob gear 225 is caused to freely rotate, both shaft 260 and actuation rod 280 are caused to simultaneously translate longitudinally relative to handle 210 in a direction of rotation of shaft gear 224. Shaft 260 and actuation rod 280 may be caused to simultaneously translate longitudinally without a change in end separation distance during the translation, where end separation is defined longitudinally between shaft distal end 242 and actuation rod distal end 262, as shown for example in the series of FIGS. 2L-2N.

In the length adjustment configuration, the mechanism to selectively prevent rotation of sun gear 216 and shaft gear 224 relative to thumb ring member 202 may be disengaged, and thus sun gear 216 and shaft gear 224 may rotate relative to thumb ring member 202 and about bearing shaft 223, as is shown in FIGS. 2P and 2Q.

In the length adjustment configuration, due to the nature of the described planetary gear mechanism, and, as shown in FIGS. 2P and 2Q, when knob gear 225 is caused to freely rotate, for example due to the user rotating control knob 226, ring gear 212 is caused to rotate in a same direction as knob gear 225. As shown in FIG. 2P, when knob gear 225 is caused to rotate in a counter-clockwise direction, knob gear teeth 225a engage with shaft gear teeth 224a and cause shaft gear 224 to turn in a clockwise direction about bearing shaft 223 and relative to thumb ring member 202. That rotation of shaft gear 224 is transferred to sun gear 216, which also rotates in a clockwise direction about bearing shaft 223 and relative to thumb ring member 202. Sun gear teeth 216a engage with planet gear teeth 213a, 214a, 215a, causing planet gears 213, 214, 215 to rotate about pins 220, 221, 222 in a counter-clockwise direction. Assuming thumb ring member 202 is not being pivoted relative to finger ring member 204, Y-brackets 218, 219 do not rotate relative to bearing shaft 223. The engagement of rotating planet gear teeth 213a, 214a, 215a with ring gear inner teeth 212b causes ring gear 212 to rotate about bearing shaft 223 in a counter-clockwise direction. Because ring gear outer teeth 212a engage with actuation rod teeth 276, and actuation rod 280 is able to translate longitudinally relative to handle 210, the counter-clockwise rotation of ring gear 212 causes actuation rod 280 to longitudinally translate such that actuation rod distal end 262 moves closer to handle 210 and actuation rod proximal end 264 moves farther from handle 210. Meanwhile, the rotation of knob gear 225 that is causing the ring gear 212 to rotate, and thus causing the actuation rod to translate, is also causing shaft 260 to translate in the same direction, because knob gear teeth 225 also engages shaft gear teeth 258, and shaft 260 is able to translated longitudinally with respect to handle 210. Thus rotation of knob gear 225 in a counter-clockwise direction also causes shaft 260 to longitudinally translate, such that shaft distal end 242 moves closer to handle 210 and shaft proximal end 244 moves farther from handle 210.

Similarly, as shown in FIG. 2Q, when knob gear 225 is caused to rotate in a clockwise direction, knob gear teeth 225a engage with shaft gear teeth 224a and cause shaft gear 224 to turn in a counter-clockwise direction about bearing shaft 223 and relative to thumb ring member 202. That rotation of shaft gear 224 is transferred to sun gear 216, which also rotates in a counter-clockwise direction about bearing shaft 223 and relative to thumb ring member 202. Sun gear teeth 216a engage with planet gear teeth 213a, 214a, 215a, causing planet gears 213, 214, 215 to rotate about pins 220, 221, 222 in a clockwise direction. Assuming thumb ring member 202 is not being pivoted relative to finger ring member 204, Y-brackets 218, 219 do not rotate relative to bearing shaft 223. The engagement of rotating planet gear teeth 213a, 214a, 215a with ring gear inner teeth 212b causes ring gear 212 to rotate about bearing shaft 223 in a clockwise direction. Because ring gear outer teeth 212a engage with actuation rod teeth 276, and actuation rod 280 is able to longitudinally translate relative to handle 210, the clockwise rotation of ring gear 212 causes actuation rod 280 to longitudinally translate such that actuation rod distal end 262 moves farther from handle 210 and actuation rod proximal end 264 moves closer to handle 210. Meanwhile, the rotation of knob gear 225 that is causing the ring gear 212 to rotate, and thus causing the actuation rod to translate, is also causing shaft 260 to translate in the same direction, because knob gear teeth 225 also engage shaft gear teeth 258, and shaft 260 is able to longitudinally translate relative to handle 210. Thus rotation of knob gear 225 in a clockwise direction also causes shaft 260 to longitudinally translate, such that shaft distal end 242 moves farther from handle 210 and shaft proximal end 244 moves closer to handle 210.

In this way, operating the length adjustment mechanism when the laparoscopic instrument 200 is in the length adjustment configuration allows the user to adjust a shaft length, where the shaft length is defined between the handle 210 and the shaft distal end 242. It also allows the user to simultaneously adjust an actuation rod length, where the actuation rod length is defined longitudinally between the handle 210 and the actuation rod distal end 262. As recognized by those skill in the art, with proper gearing ratios in gearing mechanism 240, e.g. a 1:1 ratio between knob gear 225 and ring gear 212, this allows the user to adjust the actuation rod length and the shaft length without changing an end separation distance defined longitudinally between shaft distal end 242 and actuation rod distal end 262.

Although the description of laparoscopic instrument 200 above discusses using control knob 226 to rotate knob gear 225, alternative structures could be used, for example a dial, release, switch and electric motor, or others suitable in the art. Additionally, based on the present disclosure, those skilled in the art may recognize alternative arrangements to gear mechanism 240 that would provide a similar result, for example by otherwise causing one gear or structure to engage with and translate shaft 260 and another gear or structure to engage with and translate actuation rod 280. Such structures could be actuated using a knob, a dial, release, switch and electric motor, or others suitable in the art.

Moreover, because many of the mechanisms for preventing unintended length adjustment described above can work without acting directly on control knob 226, in some embodiments, control knob 226 might be omitted, while retaining the other parts of gear mechanism 240. Then, in order to adjust shaft length and actuation rod length, the user could grasp shaft 260 directly and push or pull shaft 260 until the desired shaft length and actuation rod length is attained. For example, the user could hold handle 210 and depress an adjustment unlatching button with one hand, move shaft 260 and actuation rod 280 to a desired length with the other hand, and release the adjustment unlatching button to lock shaft 260 and actuation rod 280 at the selected position. In such embodiments, a specific feature might be coupled to shaft proximal end 244 to improve grip.

Additionally, because shaft 260 and actuation rod 280 are not connected to handle 210 at a fixed point, laparoscopic instrument 200 can also provide a "take-apart" functionality, allowing a user to partially disassemble laparoscopic instrument 200 between surgeries for better access to interior areas for cleaning. For example, by adjusting shaft length and actuation rod length beyond the longest setting, gear mechanism 240 would release shaft 260 and actuation rod 280 from handle 210. Once freed from handle 210, shaft 260 and actuation rod 280 could be separated via understood methods of disconnecting the fixed parts of an end effector 290 from a shaft tube and/or actuation rod. A release mechanism could be included to prevent a user from unintentionally releasing shaft 260 and actuation rod 280 from handle 210. In some embodiments, gear mechanism 240 may be separable from handle 210 for cleaning purposes, for example after shaft 260 and actuation rod 280 have been released from handle 210.

Overview of Laparoscopic Instrument 300

Figure 3:
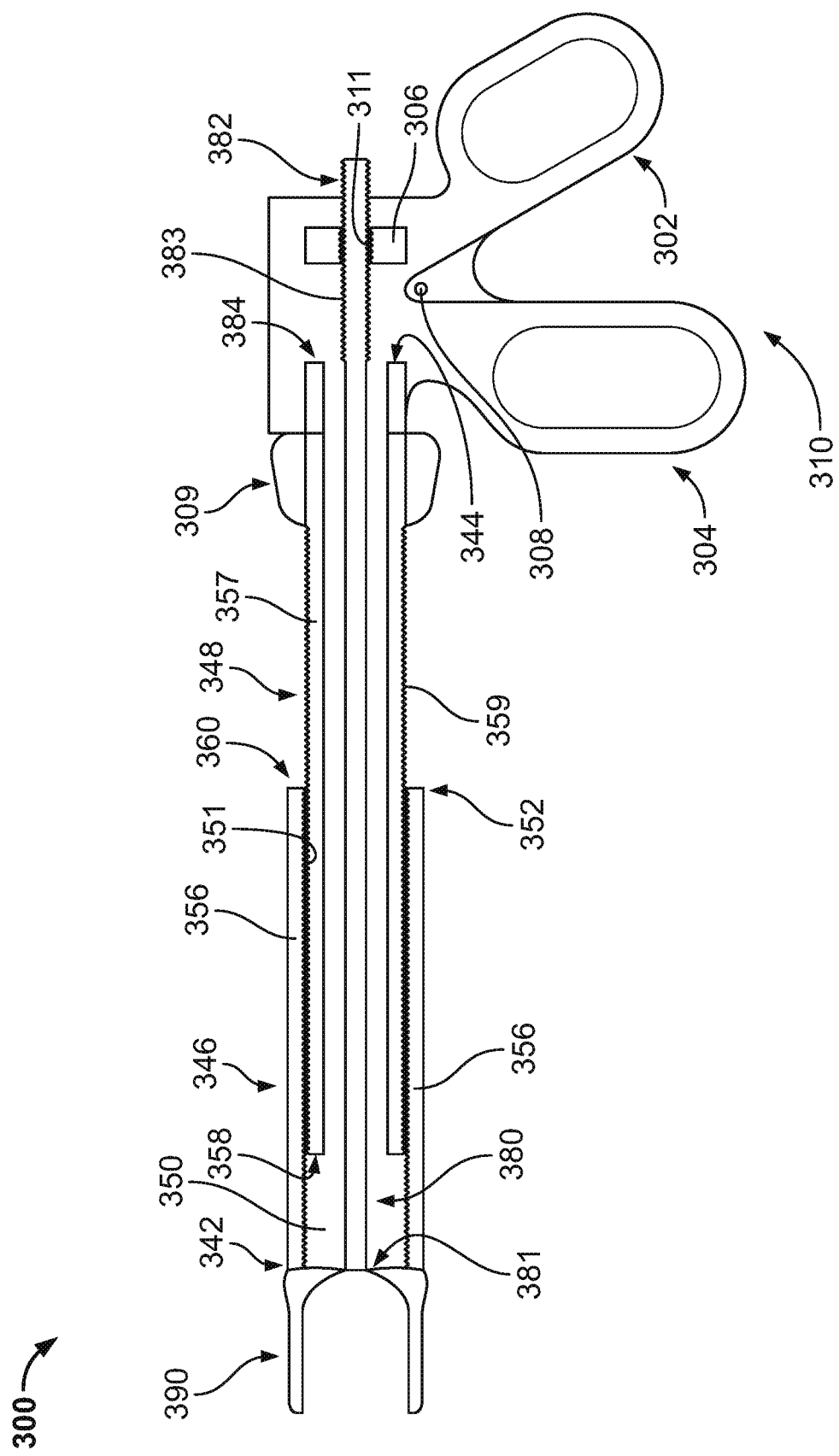
FIG. 3 shows a longitudinal sectional view of a second embodiment of a laparoscopic instrument.

A laparoscopic instrument 300 is described with reference to FIG. 3. FIG. 3 is a longitudinal section view of laparoscopic instrument 300. Laparoscopic instrument 300 is an adjustable length laparoscopic instrument. Laparoscopic instrument 300 includes handle 310, shaft 360, actuation rod 380, and end effector 390. Components of shaft 360, actuation rod 380, and handle 310 can act as a length adjustment mechanism for laparoscopic instrument 300. Components of shaft 360, actuation rod 380, and handle 310 also can be used to cause actuation rod 380 to translate longitudinally relative to shaft 360 to actuate end effector 390.

Handle 310 includes a thumb ring member 302 (commonly referred to as a "thumb bow") pivotably attached to a finger ring member 304 (commonly referred to as a "finger bow") via pin 308 in a manner recognized by those skilled in the art. Thumb ring member 302 includes threaded cage 306 defining internal threads 311. Handle 310 also includes shaft rotation knob 309 coupled to a front end of handle 310 such that shaft rotation knob 309 can rotate about a longitudinal axis of shaft 360 and actuation rod 380.

Shaft 360 extends from a distal shaft end 342 to a proximal shaft end 344. Shaft 360 includes a distal shaft section 346 and a proximal shaft section 348. Distal shaft section 346 includes a generally tubular wall 356 with an inner surface defining a lumen 350 extending from distal shaft end 342 to distal shaft section proximal end 352. The inner surface of tubular wall 356 is provided with internal threads 351.

Proximal shaft section 348 includes a generally tubular wall 357 with an inner surface defining a lumen 353 extending from proximal shaft section distal end 358 to shaft proximal end 344. The external surface of tubular wall 357 is provided with external threads 359 extending from a front end of rotation knob 309 to proximal shaft section distal end 358. Distal shaft section internal threads 351 are engageable in a complementary manner with proximal shaft section external threads 359, such that distal shaft section 346 can be screwed onto and off of proximal shaft section 348 in a manner causing distal shaft section 346 to longitudinally translate relative to proximal shaft section 348. End effector 390 is coupled to shaft distal end 342. Proximal shaft end 344 is coupled to finger ring member 304 such that proximal shaft section 348 can rotate about its longitudinal axis relative to finger ring member 304. Rotation knob 309 is coupled to shaft 360 towards proximal shaft end 344 such that the user can rotate rotation knob 309 to rotate proximal shaft section 348 about its longitudinal axis relative to finger ring member 304.

Actuation rod 380 is a generally cylindrical member extending from actuation rod distal end 381 to actuation rod proximal end 382. An external surface of actuation rod 380 is provided with external threads 383 extending from actuation rod proximal end 382 to intermediate point 384. Actuation rod external threads 383 are engageable in a complementary manner with threaded cage internal threads 311, such that actuation rod 380 can be screwed into and out of threaded cage internal threads 311 in a manner causing actuation rod 380 to longitudinally translate relative to handle 310. End effector 390 is coupled to actuation rod distal end 381 such that actuation rod 380 does not rotate relative about its longitudinal axis relative to end effector 390.

Operation of Laparoscopic Instrument 300

To simultaneously adjust shaft length of shaft 360 and actuation rod length of actuation rod 380, a user may grab rotation knob 309 and at least one of end effector 390 or distal shaft section 346 and turn one relative to the other. With rotation in a first direction, distal shaft section internal threads 351 will engage with proximal shaft section external threads 359 so that distal shaft section 346 is screwed onto proximal shaft section 348, thus increasing shaft length of shaft 360. With rotation in a second opposite direction, distal shaft section internal threads 351 will engage with proximal shaft section external threads 359 so that distal shaft section 346 is screwed off of proximal shaft section 348, thus decreasing shaft length of shaft 360. Additionally, because actuation rod distal end 381 is coupled to end effector 390 so they do not rotate relative to each other about the longitudinal axis of actuation rod 380, and end effector 390 is similarly coupled to distal shaft end 342, the user's rotation applied to end effector 390 or distal shaft section 346 is translated to actuation rod 380. Accordingly, when rotation is applied that screws distal shaft section 346 off of proximal shaft section 348, threaded cage internal threads 311 and actuation rod external threads 383 cause actuation rod 380 to longitudinally translate away from handle 310 simultaneously with distal shaft section 346. Similarly, when rotation is applied that screws distal shaft section 346 onto proximal shaft section 348, threaded cage internal threads 311 and actuation rod external threads 383 cause actuation rod 380 to longitudinally translate towards handle 310 simultaneously with distal shaft section 346. Moreover, because threaded cage 306 otherwise functions similarly to known ball cages, pivoting thumb ring member 302 relative to finger ring member 304 causes actuation rod 380 to longitudinally translate relative to handle 310 and shaft 360 so as to operate end effector 390 at any length setting for which threaded cage internal threads 311 are able to engage actuation rod external threads 383.

Overview of Laparoscopic Instrument 400

Figure 4:
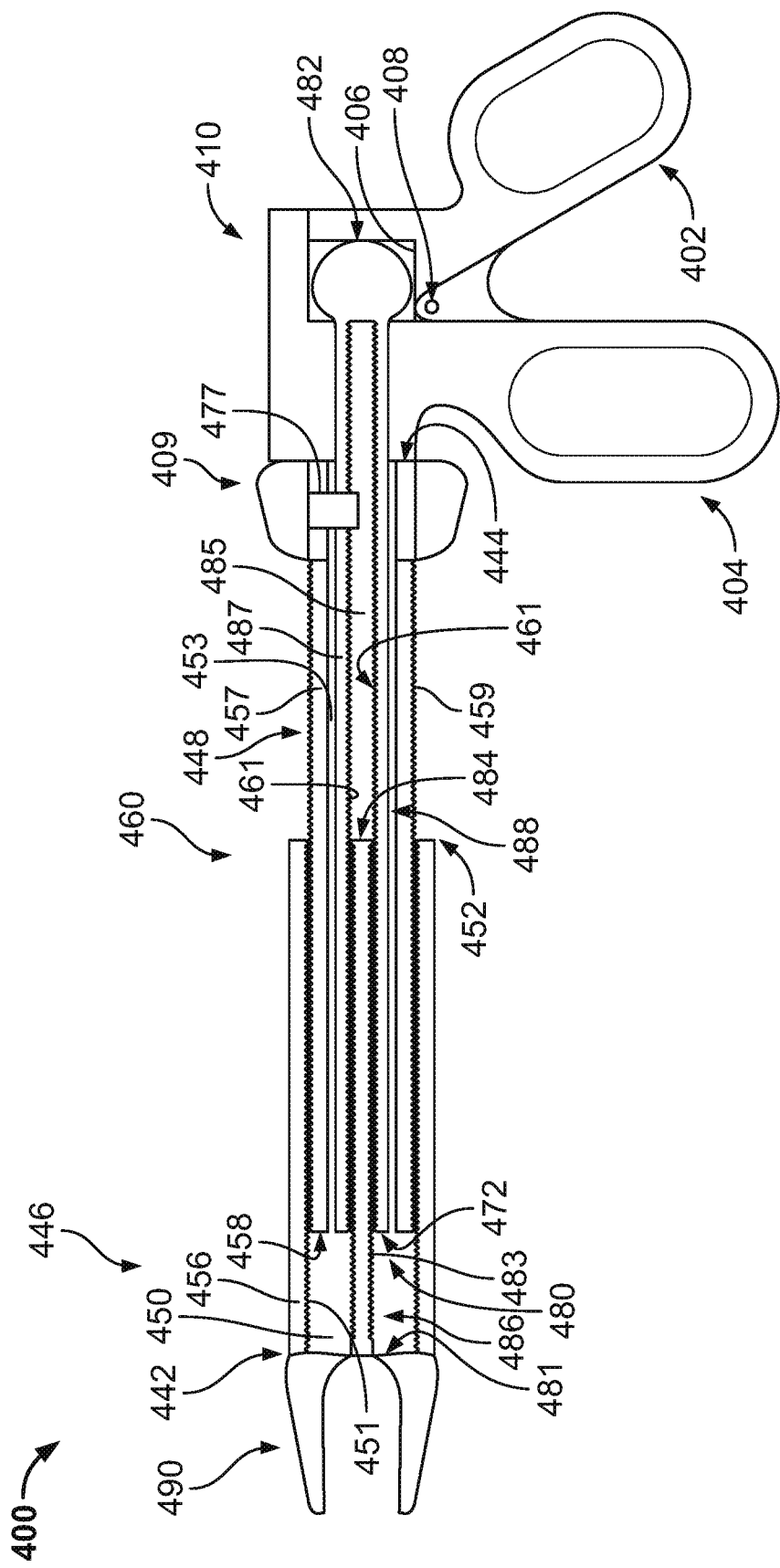
FIG. 4 shows a longitudinal sectional view of a third embodiment of a laparoscopic instrument.

A laparoscopic instrument 400 is described with reference to FIG. 4. FIG. 4 is a longitudinal sectional view of laparoscopic instrument 400. Laparoscopic instrument 400 is an adjustable length laparoscopic instrument. Laparoscopic instrument 400 includes handle 410, shaft 460, actuation rod 480, and end effector 490. Components of shaft 460, actuation rod 480, and handle 410 can act as a length adjustment mechanism for laparoscopic instrument 400. Components of shaft 460, actuation rod 480, and handle 410 also can be used to cause actuation rod 480 to translate longitudinally relative to shaft 460 to actuate end effector 490.

Handle 410 includes a thumb ring member 402 (commonly referred to as a "thumb bow") pivotably attached to a finger ring member 404 (commonly referred to as a "finger bow") via pin 408 in a manner recognized by those skilled in the art. Thumb ring member 402 includes ball cage 406. Handle 410 also includes shaft rotation knob 409 coupled to a front end of handle 410 such that shaft rotation knob 409 can rotate about a longitudinal axis of shaft 460 and actuation rod 480.

Shaft 460 extends from a distal shaft end 442 to a proximal shaft end 444. Shaft 460 includes a distal shaft section 446 and a proximal shaft section 448. Distal shaft section 446 includes a generally tubular wall 456 with an inner surface defining a lumen 450 extending from distal shaft end 442 to distal shaft section proximal end 452. The inner surface of tubular wall 456 is provided with internal threads 451.

Proximal shaft section 448 includes a generally tubular wall 457 with an inner surface defining a lumen 453 extending from proximal shaft section distal end 458 to shaft proximal end 444. The external surface of tubular wall 457 is provided with external threads 459 extending from a front end of rotation knob 409 to proximal shaft section distal end 458. Distal shaft section internal threads 451 are engageable in a complementary manner with proximal shaft section external threads 459, such that distal shaft section 446 can be screwed onto and off of proximal shaft section 448 in a manner causing distal shaft section 446 to longitudinally translate relative to proximal shaft section 448. End effector 490 is coupled to shaft distal end 442. Proximal shaft end 444 is coupled to finger ring member 404 such that proximal shaft section 448 can rotate about its longitudinal axis relative to finger ring member 404. Rotation knob 409 is coupled to shaft 460 towards proximal shaft end 444 such that the user can rotate rotation knob 409 to rotate proximal shaft section 448 about its longitudinal axis relative to finger ring member 404.

Actuation rod 480 extends from actuation rod distal end 481 to actuation rod proximal end 482. Actuation rod 480 includes a distal actuation rod section 486 and a proximal actuation rod section 488. Distal actuation rod section 486 is a generally cylindrical member having an external surface provided with external threads 483 extending from actuation rod distal end 481 to distal actuation rod section proximal end 484. Proximal actuation rod section 486 includes a generally tubular wall 487 defining a lumen 485 extending from proximal actuation rod section distal end 472 to towards actuation rod proximal end 482. The inner surface of tubular wall 487 is provided with inner threads 461. Actuation rod proximal end 482 is a ball configured to be captured by ball cage 406. Distal actuation rod section external threads 483 are engageable in a complementary manner with proximal actuation rod section inner threads 461, such that distal actuation rod section 486 can be screwed into and out of proximal actuation rod section inner threads 461 in a manner causing distal actuation rod section 486 to longitudinally translate relative to handle 410 and proximal actuation rod section 488. End effector 490 is coupled to actuation rod distal end 481 such that distal actuation rod section 486 does not rotate relative about its longitudinal axis relative to end effector 490.

In some embodiments, rotation knob 409 may include a key 477 keyed to slots in a proximal portions of actuator rod 480 and shaft 460. This may ensure that actuator rod 480 and shaft 460 remain in a same relative rotational position when rotation knob 409 is used to rotate end effector 490 by rotating shaft 460, while also allowing actuator rod 480 to translate longitudinally relative to shaft 460 and handle 410 when the user operates end effector 490.

Operation of Laparoscopic Instrument 400

To simultaneously adjust shaft length of shaft 460 and actuation rod length of actuation rod 480, a user may grab rotation knob 409 and at least one of end effector 490 or distal shaft section 446 and turn one relative to the other. With rotation in a first direction, distal shaft section internal threads 451 will engage with proximal shaft section external threads 459 so that distal shaft section 446 is screwed onto proximal shaft section 448, thus increasing shaft length of shaft 460. With rotation in an opposite second direction, distal shaft section internal threads 451 will engage with proximal shaft section external threads 459 so that distal shaft section 446 is screwed off of proximal shaft section 448, thus decreasing shaft length of shaft 460. Additionally, because actuation rod distal end 481 is coupled to end effector 490 so they do not rotate relative to each other about the longitudinal axis of actuation rod 480, and end effector 490 is similarly coupled to distal shaft end 442, the user's rotation applied to end effector 490 or distal shaft section 446 is translated to distal actuation rod section 486. Accordingly, when rotation is applied that screws distal shaft section 446 off of proximal shaft section 448, proximal actuation rod section inner threads 461 and distal actuation rod section external threads 483 cause actuation rod distal end 481 to longitudinally translate away from handle 410 simultaneously with distal shaft section 446. Similarly, when rotation is applied that screws distal shaft section 446 on to proximal shaft section 448, proximal actuation rod section inner threads 461 and distal actuation rod section external threads 483 cause actuation rod distal end 481 to longitudinally translate towards handle 410 simultaneously with distal shaft section 446. Moreover, because the engagement between proximal actuation rod section inner threads 461 and distal actuation rod section external threads 483 cause actuation rod 480 to change length as much as shaft 460, the ball at actuation rod proximal end 482 remains located in ball cage 406 regardless of the instrument's length setting. Thus pivoting thumb ring member 402 relative to finger ring member 404 causes actuation rod 480 to longitudinally translate relative to handle 410 and shaft 460 to operate end effector 490 at any length setting.

Laparoscopic Instrument 500

Figure 5:
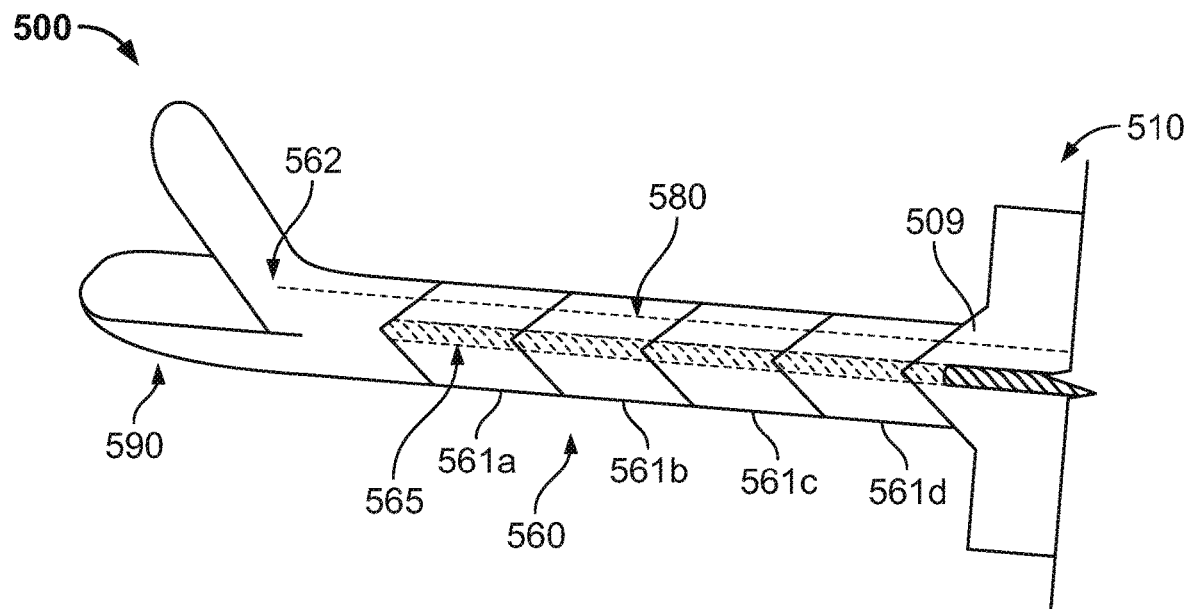
FIG. 5 shows a schematic view of a fourth embodiment of a laparoscopic instrument in a first configuration.
Figure 5A:
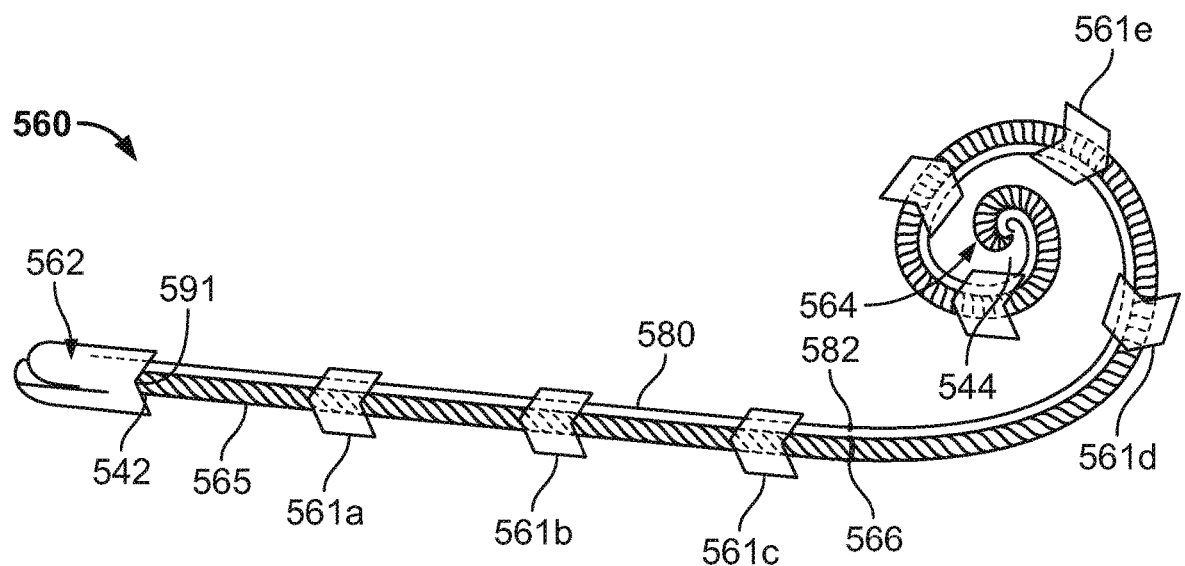
FIG. 5A shows a schematic view of the laparoscopic instrument of FIG. 5 in a second configuration with a handle removed.

A laparoscopic instrument 500 is described with reference to FIGS. 5 and 5A. FIG. 5 is a schematic view of laparoscopic instrument 500 in a generally tubular configuration. Laparoscopic instrument 500 is an adjustable length laparoscopic instrument. Laparoscopic instrument 500 includes handle 510, shaft 560, actuation rod 580, and end effector 590. Handle 510 is removable, as shown in FIG. 5A. FIG. 5A is a schematic view of instrument 500 in a substantially flexible and partially wound configuration. Components of shaft 560, actuation rod 580, and handle 510 can act as a length adjustment mechanism for laparoscopic instrument 500. Components of shaft 560, actuation rod 580, and handle 510 also can be used to cause actuation rod 580 to translate longitudinally relative to shaft 560 to actuate end effector 590.

Shaft 560 is formed of a plurality of links 561a, 561b, 561c, 561d, 561e mounted on elongated shaft member 565. Elongated shaft member 565 is flexible such that in some configurations it can be wound up, for examples as shown in FIG. 5A. Elongated shaft member 565 includes a plurality of tensioner beads, such as tensioner bead 566, each fixedly coupled to elongated shaft member 565 and located in a spaced apart manner along its length. Links 561a, 561b, 561c, 561d, 561e are capable of longitudinally translating relative to each other along elongated shaft member 565, as shown in FIG. 5A. Links 561a, 561b, 561c, 561d, 561e may be generally chevron-shaped in cross section, such that they can stack together as shown in FIG. 5. Each link 561a, 561b, 561c, 561d, 561e may include a respective lumen, such that when stacked together, links 561a, 561b, 561c, 561d, 561e may as a unit define a substantially rigid generally tubular structure with a longer internal lumen. Proximal end 544 of elongated shaft member 565 passes back through the respective lumens of links 561a, 561b, 561c, 561d, 561e and elongated shaft member distal end 542 fixedly couples to a proximal end 591 of end effector 590. End effector proximal end 591 may be shaped so as to stack with link 561a.

Actuation rod 580 is flexible such that in some configurations it can be wound up, as seen for example in FIG. 5A. Actuation rod 580 includes an actuation rod distal end 562 coupled to end effector 590 and an actuation rod proximal end 564 passed back through the respective lumens of links 561a, 561b, 561c, 561d, 561e. Actuation rod 580 includes a plurality of actuation beads, such as actuation bead 582, each fixedly coupled to actuation rod 580 and located in a spaced apart manner along its length.

Handle 510 includes on its distal end nose 509 that can engage with a proximal edge of whichever of links 561a, 561b, 561c, 561d, 561e is immediately distal to handle 510. Handle 510 also includes in its interior a structure configured to engage tensioner beads, e.g. tensioner bead 566, such that when elongated shaft member 565 is pulled distally to cause links to stack against nose 509 and form a substantially rigid generally tubular structure, as depicted in FIG. 5, the tension that keeps the links stacked together is retained. Handle 510 also includes in its structure an actuator configured to engage an exposed actuation bead, e.g. actuation bead 582, to apply tension to actuator rod 580 and thereby cause actuation rod 580 to translate longitudinally relative to shaft 560 and operate end effector 590, for example as shown in FIG. 5.

In use, shaft length of laparoscopic instrument 500 is changed by sliding a desired number of links either into handle 510 to shorten shaft length, or out of handle 510 to increase shaft length, and then engaging a tensioner bead, e.g. tensioner bead 566, within the handle such that the links outside of the handle form the substantially rigid generally tubular structure discussed above. Proximal portions of elongated shaft member 565 and actuation rod 580 that support links positioned inside the handle may also be positioned within handle 510. To store proximal portions of elongated member 565 and actuation rod 580 links, e.g. link 561e, within handle 510, proximal portions of elongated shaft member 565 and actuation rod 580 may be wound up along with one or more separated links, such as link 561e, for example as shown in FIG. 5A, and the wound structure can be stored within handle 510.

In some embodiments, to change the shaft length of laparoscopic instrument 500, handle 510 includes two sections, for example in a clamshell configuration, that can be snapped together to surround proximal portions of elongated shaft member 565 and actuation rod 580 and one or more separated links, e.g. link 561e. In these embodiments, nose 509 may be split between the two sections of handle 510, so that when the two sections of handle 510 are snapped together, nose 509 provides a surface upon which a proximal-most outside link, e.g. link 561d, can apply pressure when tension is applied to elongated shaft member 565. That pressure may place laparoscopic instrument 500 in the substantially rigid generally tubular structure discussed above in connection with FIG. 5. Nose 509 may thus include a distally facing nose opening that receives elongated shaft member 565 and actuation rod 580 therethrough and allows them to pass into handle 510, but that is too small to receive links 561a, 561b, 561c, 561d, 561e therethrough and allow them to pass into handle 510. FIG. 5 depicts such an embodiment with one section of handle 510 removed for clarity.

In other embodiments, handle 510 may not be snapped together to surround proximal portions of elongated shaft member 565 and actuation rod 580 and one or more separated links. For example, in some embodiments, handle 510 may instead include a distally facing handle opening large enough to allow links to be withdrawn into handle 510 through the handle opening and pushed out of the handle opening and thus out of handle 510. In such embodiments, nose 509 may be implemented as a shutter that can slide between an open configuration and a closed configuration. In the open configuration, nose 509 may allow links to be withdrawn into or pushed out of handle 510 through the handle opening. In the closed configuration, nose 509 may provide a surface upon which a proximal-most link, e.g. link 561d, can apply pressure when tension is applied to elongated shaft member 565. Nose 509 may thus include a distally facing nose opening that is smaller than the handle opening and that receives elongated shaft member 565 and actuation rod 580 therethrough and allows them to pass into the handle opening, but that is too small to receive links 561a, 561b, 561c, 561d, 561e therethrough and prevents them from passing into the handle opening. In embodiments where nose 509 is implemented as a shutter, nose 509 may be attached to a distal surface of handle 510 so nose 509 can slide up and down (i.e. transversely to the longitudinal axis of shaft 560) relative to handle 510 to transition between the open configuration and the closed configuration. The distally facing nose opening may thus include a transversely facing slot so that nose 509 can slide transversely onto elongated shaft member 565 and actuation rod 580 to enter the closed configuration slide transversely and off of elongated shaft member 565 and actuation rod 580 to enter the open configuration.

In some embodiments, e.g. those in which nose 509 is implemented as a shutter that can slide between an open configuration and a closed configuration, in order to withdraw links into handle 510 and push links out of handle 510, handle 510 may further include a reeling mechanism that allows proximal portions of elongated shaft member 565, actuator rod 580, and links 561a, 561b, 561c, 561d, 561e to be reeled distally and proximally relative to handle 510 when in the open configuration. The reeling mechanism may include a reeling shaft extending transversely across handle 510 and about which proximal portions of elongated shaft member 565 and actuator rod 580 and one or more links, e.g. link 561e, can be wound. The reeling shaft may be attached to a crank lever, which may for example be similar to a fishing reel handle, and which may be rotated relative to handle 510 in a first direction in order to reel elongated shaft member 565, actuator rod 580, and links 561a, 561b, 561c, 561d, 561e in a proximal direction (i.e. towards or into handle 510), and which may be rotated relative to handle 510 in an opposite second direction in order to reel elongated shaft member 565, actuator rod 580, and links 561a, 561b, 561c, 561d, 561e in a distal direction (i.e. away from or out of handle 510).

Laparoscopic Instrument 600

Figure 6:
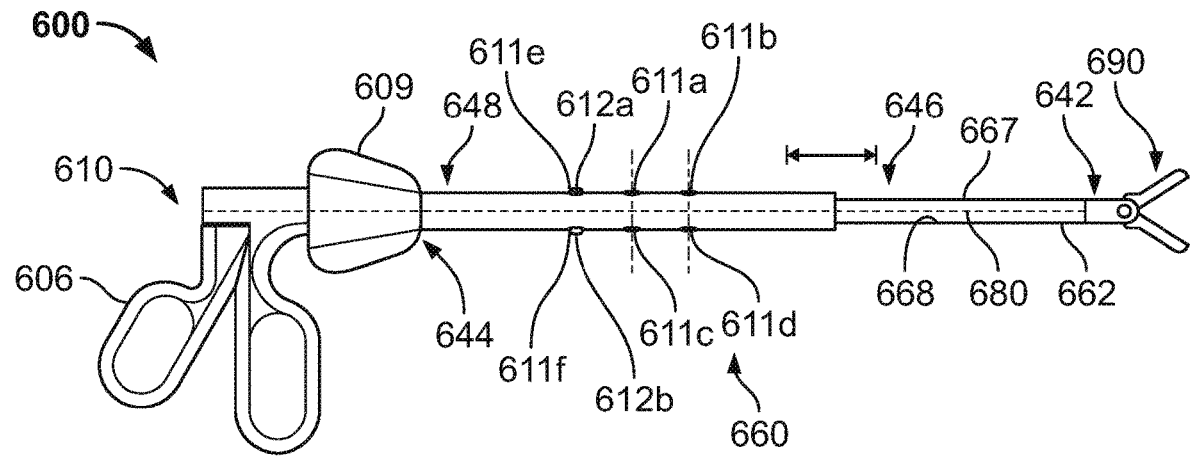
FIG. 6 shows a schematic view of a fifth embodiment of a laparoscopic instrument.
Figure 6A:
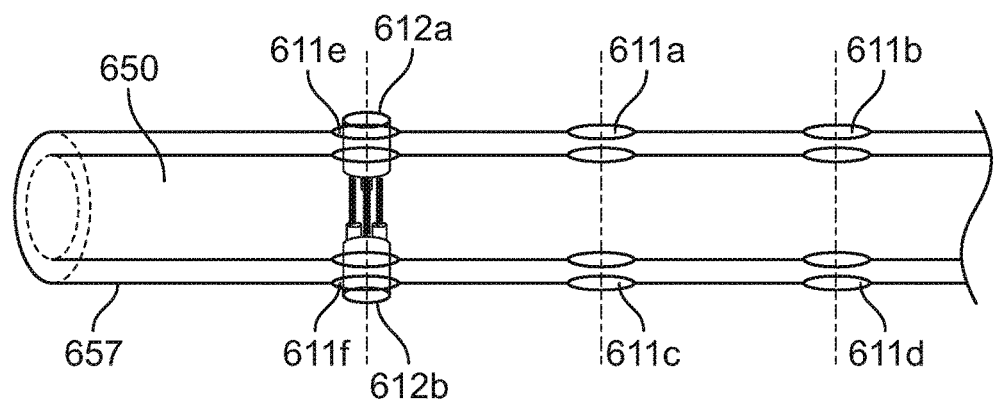
FIG. 6A shows a partial schematic view of inner and outer shaft sections of the laparoscopic instrument of FIG. 6.

A laparoscopic instrument 600 is described with reference to FIGS. 6 and 6A. FIG. 6 is a schematic view of laparoscopic instrument 600. Laparoscopic instrument 600 is an adjustable length laparoscopic instrument. Laparoscopic instrument 600 includes handle 610, shaft 660, actuation rod 680, and end effector 690. Components of shaft 660 and actuation rod 680 can act as a length adjustment mechanism for laparoscopic instrument 600. Components of shaft 660, actuation rod 680, and handle 610 also can be used to cause actuation rod 680 to translate longitudinally relative to shaft 660 to actuate end effector 690.

Shaft 660 extends from shaft proximal end 644 to shaft distal end 642, and includes an inner distal shaft section 646 and an outer proximal shaft section 648. Outer proximal shaft section 648 includes a generally tubular wall 657 defining a lumen 650 configured to receive inner distal shaft section 646 such that inner distal shaft section 646 can translate longitudinally relative to outer proximal shaft section 648. A plurality of openings 611a, 611b, 611c, 611d, 611e, 611f are formed through the generally tubular wall 657.

Inner distal shaft section 646 includes a generally tubular wall 667 defining a lumen 668. Inner distal shaft section 646 also includes detents 612a, 612b biased radially outward with respect to inner distal shaft section 646, and capable of being pushed radially inward with respect to inner distal shaft section 646. Detents 612a, 612b may be in the form of spring loaded buttons, as depicted in FIG. 6A. Generally tubular wall 667 of inner distal shaft section 646 is not shown in FIG. 6A. Generally, springs or other biasing mechanisms will be arranged such that they do not obstruct longitudinal translation of actuation rod 680 through lumen 668. Actuation rod 680 passes from a coupling at its distal end 662 with end effector 690 through lumen 668 and into handle 610.

To operate laparoscopic instrument 600, the user pushes detents 612a, 612b radially inward with respect to inner distal shaft section 646 and longitudinally translates inner distal shaft section 646 distally or proximally until detents 612a, 612b line up with pairs of openings 611a, 611b, 611c, 611d, 611e, 611f such that a desired shaft length is obtained. When detents 612a, 612b line up with a pair of openings, their radially outward bias makes them lock into the pair of openings. This telescoping configuration allows for a variety of lengths to be selected. For example, openings 611e, 611f may set a length of 24 cm, openings 611a, 611c may set a length of 36 cm, and openings 611b, 611d may set a length of 45 cm. Actuator rod 680 may be engaged with handle 610 in a variety of ways that will allow actuator rod distal end 662 to longitudinally translate during shaft length adjustment while also ensuring that the proximal end of actuator rod 680 operably aligns with the portion of the handle that actuates actuator rod 680 for operation of end effector 690.

Figure 7:
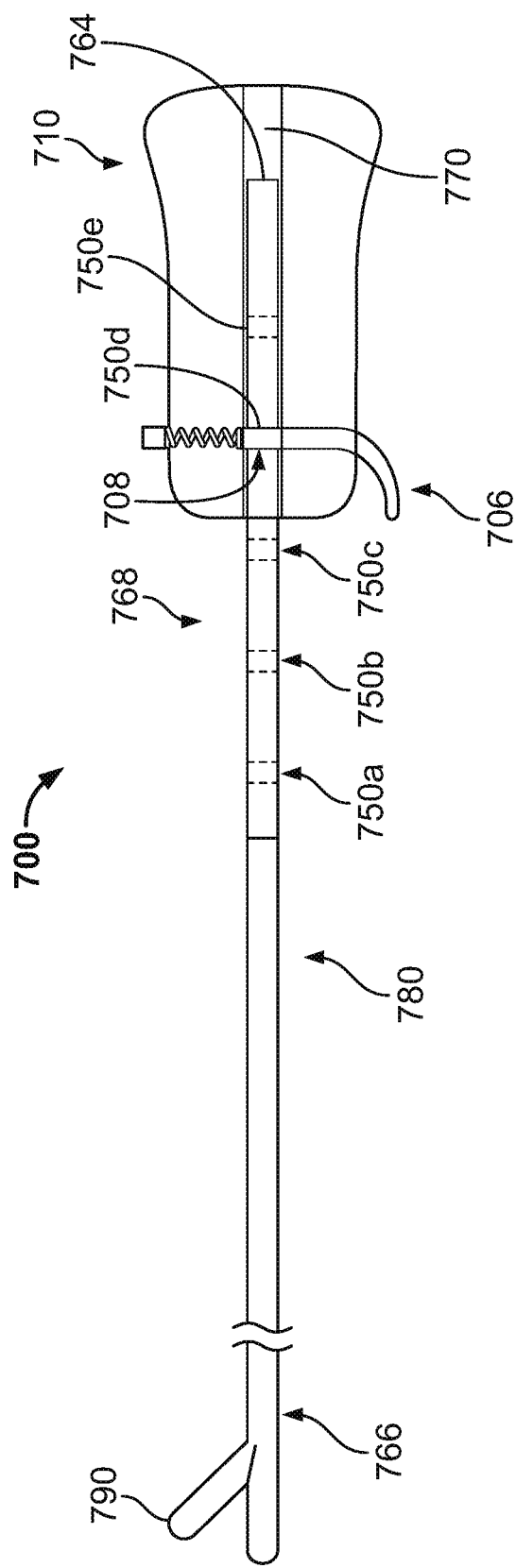
FIG. 7. shows a schematic view of a mechanism for engaging an actuation rod proximal end with a handle in adjustable length laparoscopic instruments.

FIG. 7 is a schematic view depicting an exemplary mechanism 700 for engaging an actuator rod and handle that will allow the actuator rod distal end to longitudinally translate during shaft length adjustment while also ensuring that the proximal end of the actuator rod operably aligns with the portion of the handle that actuates the actuator rod for operation of an end effector. Mechanism 700 could be implemented in laparoscopic instruments with various shaft length adjustment mechanisms, including for example a telescoping laparoscopic instrument such as laparoscopic instrument 600 discussed above. FIG. 7 depicts actuator rod 780 and handle 710. Actuator rod 780 is generally cylindrical and extends from actuator rod proximal end 764 to actuator rod distal end 766. Actuator rod distal end 766 is coupled to end effector 790. Actuator rod 780 includes a proximal actuator rod section 768. Proximal actuator rod section 768 includes a plurality of slots 750a, 750b, 750c, 750d, 750e formed radially therethrough and located at separated longitudinal positions.

Handle 710 includes a trigger 706 pivotably coupled thereto. Trigger 706 includes a pin 708 configured to enter one of slots 750a, 750b, 750c, 750d, 750e that has longitudinally translated so as to align with pin 708. As actuator rod 780 is caused by a shaft length adjustment mechanism to longitudinally translate along with a shaft, pin 708 will become aligned with and enter one of slots 750a, 750b, 750c, 750d, 750e. For example, in FIG. 7, pin 708 has become aligned with and entered slot 750d. Once pin 708 enters the aligned slot, trigger 706 can be pivoted forward and backward in handle 710 to cause actuator rod 780 to longitudinally translate relative to handle 710 and the shaft. That relative translation of actuator rod 780 allows the user to operate end effector 790 in a manner recognized by those skilled in the art. Handle 710 includes a cavity 770 that has enough excess space to contain a length of actuator rod 780 equivalent to the amount by which the shaft length can be adjusted.

Electrosurgical Considerations

In electrosurgical laparoscopic instruments, an electrode is generally put in electroconductive contact with the actuation rod so that electricity can be transmitted to the end effector. Generally, the electrode is attached to the shaft, for example as shown in FIG. 1 in connection with laparoscopic instrument 100. This configuration may become more complicated to implement in adjustable length laparoscopic instruments, including at least some described in the present disclosure. One solution to this problem may be to move the electrode so it is located directly on the proximal end of the actuator rod. This solution may be particularly beneficial in adjustable length laparoscopic instruments in which the actuator rod extends proximally from the handle, for example laparoscopic instruments 200 and 300.

Figure 8A:
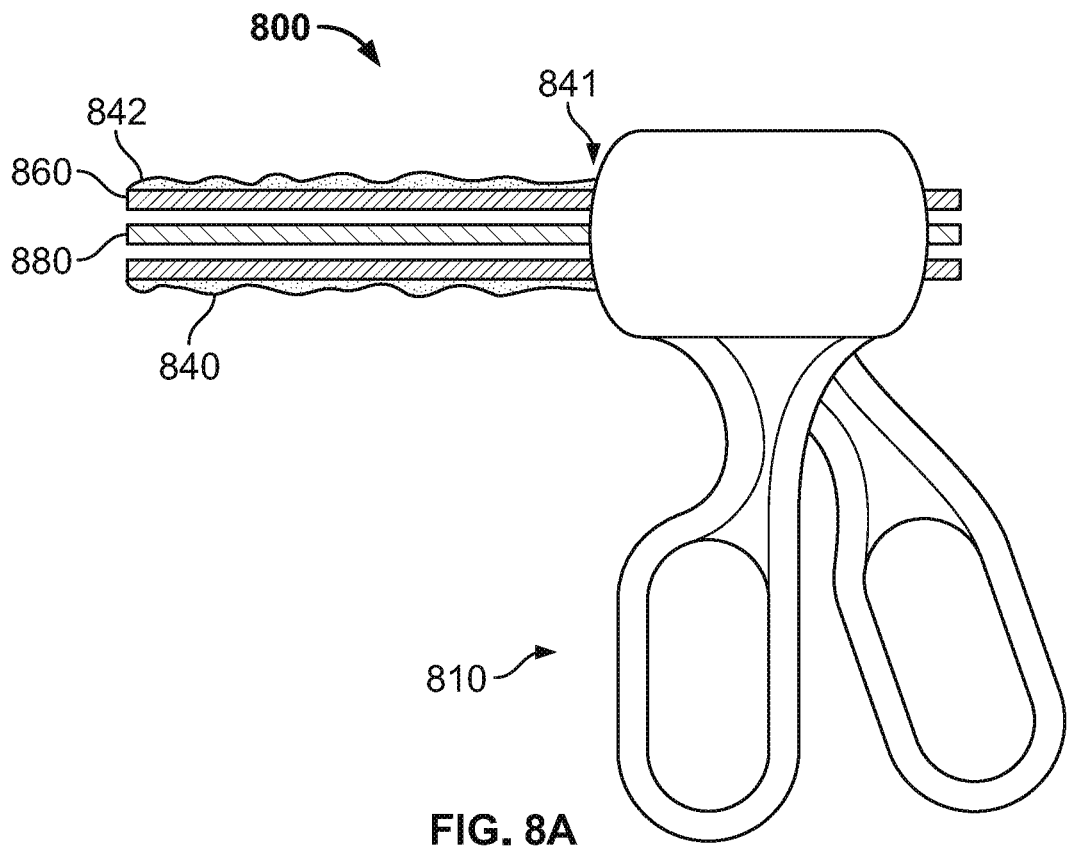
FIG. 8A shows a longitudinal sectional view of an adjustable length laparoscopic instrument with adjustable length insulation in an extended configuration.
Figure 8B:
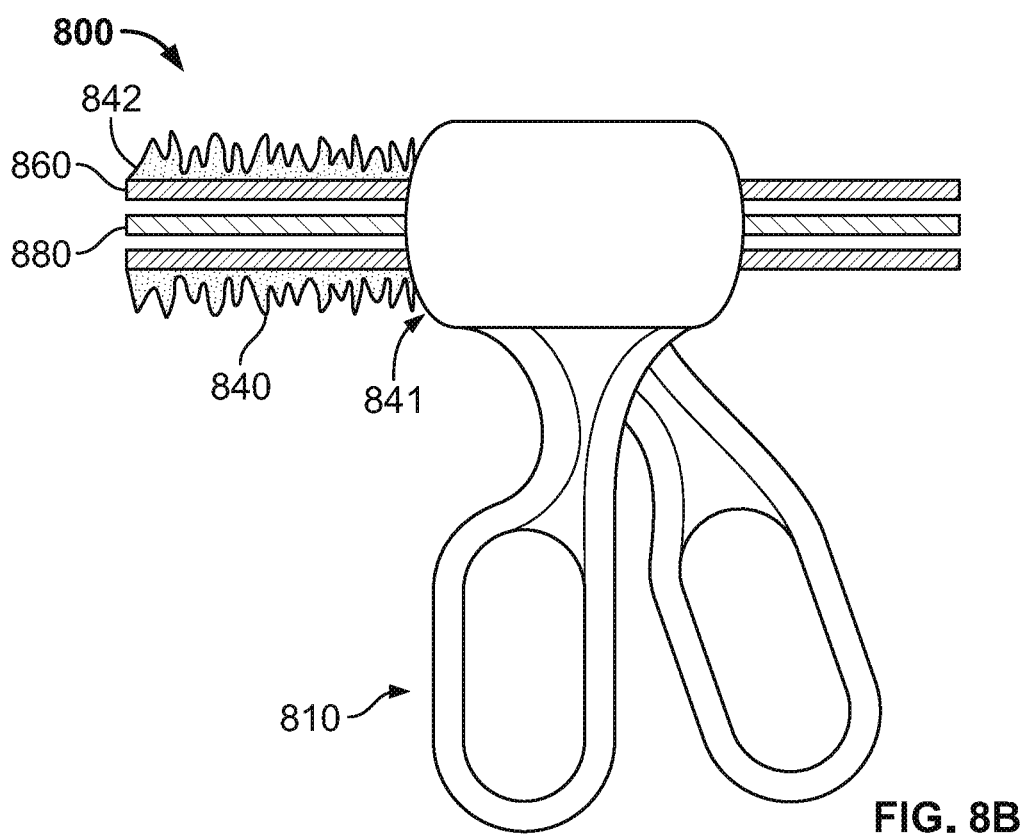
FIG. 8B shows a longitudinal sectional view of the adjustable length laparoscopic instrument of adjustable length insulation of FIG. 8A in an retracted configuration.

Additionally, exterior surfaces of electrosurgical laparoscopic instruments should generally be electrically insulated to avoid potential electrical shorts from the actuation rod through the shaft, which for example could shock the patient or user of the instrument. FIGS. 8 and 8A depict an adjustable length laparoscopic instrument 800 that includes a handle 810, a shaft 860, an actuation rod 880, and adjustable length insulation 840. Adjustable length insulation 840 has a proximal end 841 fixedly coupled to handle 810, and a distal end 842 fixedly coupled to a portion of shaft 860 distal to handle 810. Adjustable length insulation 840 is able to extend as shaft 860 is longitudinally translated away from handle 810, as shown in a progression from FIG. 8B to FIG. 8A. Adjustable length insulation 840 is also able to contract as shaft 860 is longitudinally translated towards handle 810, as shown in a progression from FIG. 8A to 8B. Adjustable length insulation 840 may have an accordion configuration or be flexible so it has the ability to extend and contract. Adjustable length insulation distal end 842 may be coupled at a distal end of shaft 860, or may be coupled proximal to the distal end of shaft 860 such that adjustable length insulation 840 joins standard insulation more tightly conforming to the outer contours of shaft 860. This latter option may allow a distal portion of laparoscopic instrument 800 to more easily be passed through a standard trocar or access port into the patient.

Figure 9:
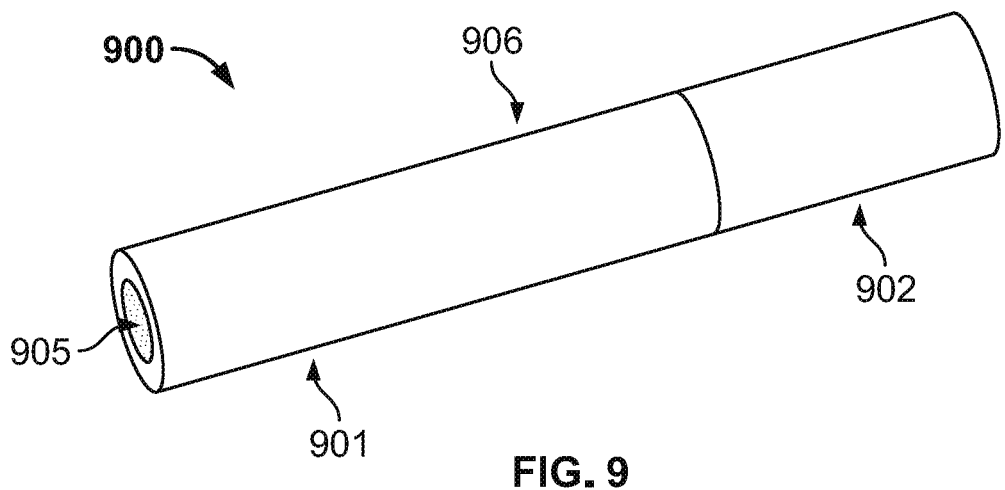
FIG. 9 shows a perspective view of insulated laparoscopic instrument components in a shortened configuration.
Figure 9A:
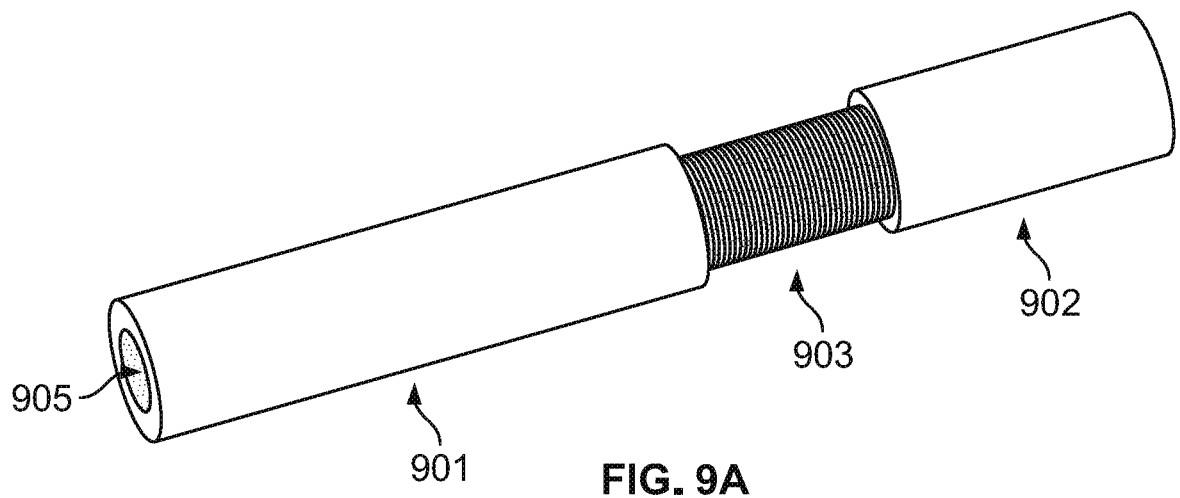
FIG. 9A shows a perspective view of the insulated laparoscopic instrument components of FIG. 9 in a lengthened configuration
Figure 9B:
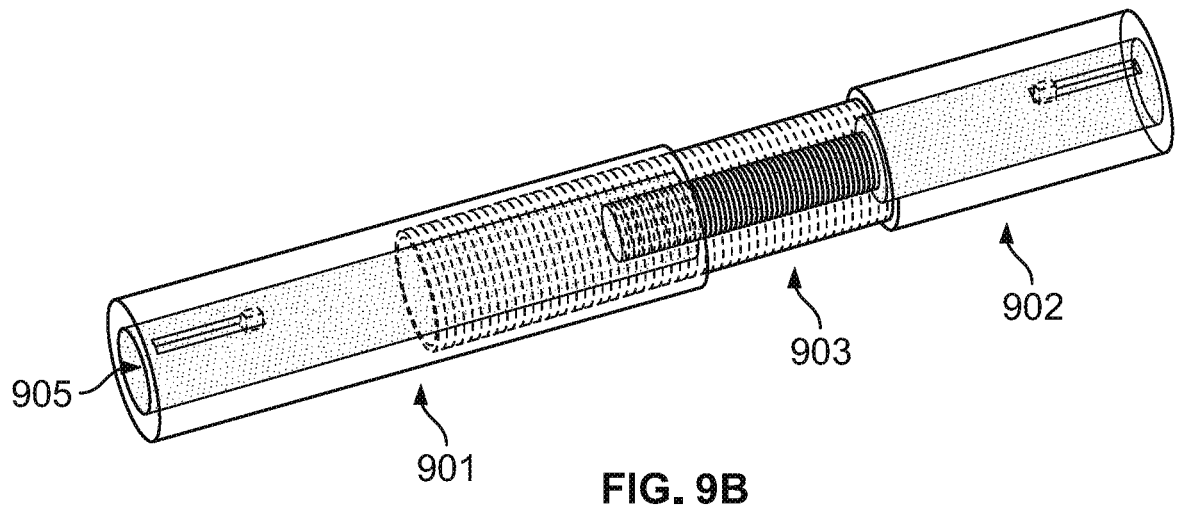
FIG. 9B shows a perspective view of the insulated laparoscopic instrument components of FIG. 9 in the lengthened configuration of FIG. 9A, with the insulating shaft shown in outline to reveal the actuation rod and internal surface aspects of the insulating shaft.
Figure 9C:
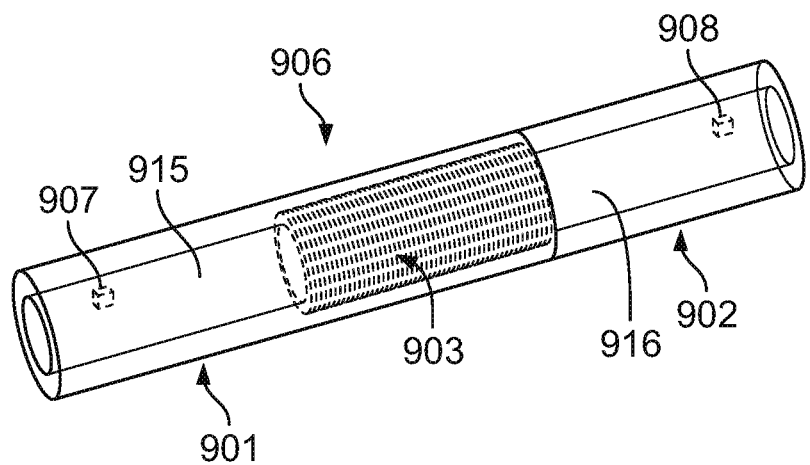
FIG. 9C shows a perspective view of the insulating shaft in a shortened configuration and in outline to reveal internal aspects.
Figure 9D:
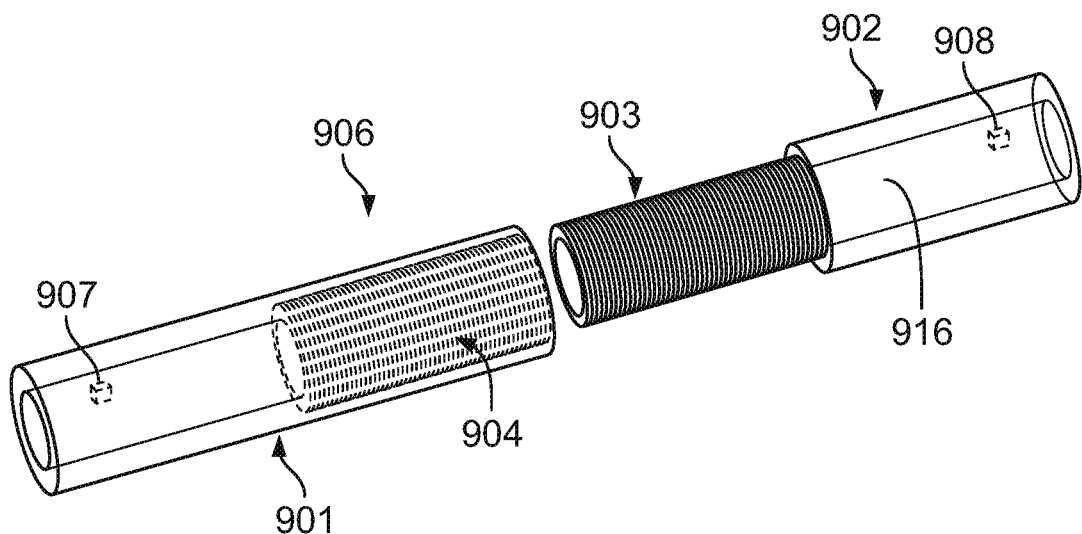
FIG. 9D shows a perspective view of the insulating shaft in a disassembled configuration and in outline to reveal internal aspects.
Figure 9E:
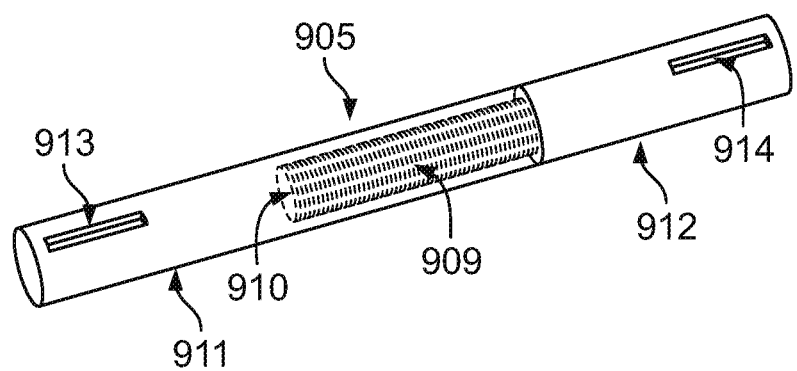
FIG. 9E shows a perspective view of the actuation rod in a shortened configuration and in outline to reveal internal aspects.
Figure 9F:
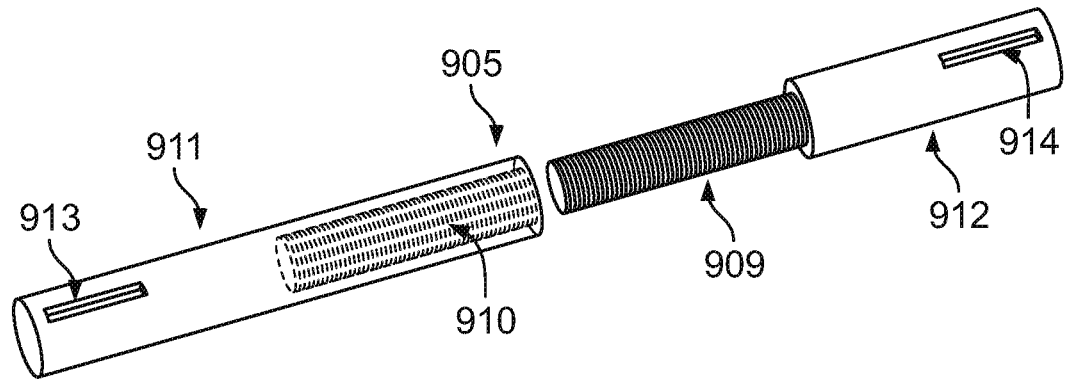
FIG. 9F shows a perspective view of the actuation rod in a disassembled configuration and in outline to reveal internal aspects.

A second embodiment of an insulation configuration for adjustable length laparoscopic instruments is depicted in FIGS. 9-9F. Laparoscopic instrument components 900 include shaft 906 and actuation rod 905. FIG. 9 depicts shaft 906 and actuation rod 905 assembled together in a shortest configuration. FIG. 9A depicts shaft 906 and actuation rod 905 assembled together in a longer configuration. FIG. 9B depicts shaft 906 and actuation rod 905 assembled together in a longer configuration, with shaft 906 illustrated only in outline so that certain internal details can be seen.

Shaft 906 includes first shaft member 901 and second shaft member 902. First shaft member 901 is a generally tubular member and includes internal threads 904 formed on an inner surface of lumen 915. First shaft member 901 also includes a key 907 projecting into lumen 915. Second shaft member 902 is a generally tubular member and includes external threads 903 formed on a portion thereof. Second shaft member 902 also includes a lumen 916 and a key 908 projecting into lumen 916. External threads 903 are configured to engage in a complementary manner with internal threads 904 such that second shaft member 902 can be screwed into first shaft member 901, for example as seen in FIG. 9C, or out of first shaft member 901, for example as seen in FIG. 9D. Both first shaft member 901 and second shaft member 902 are formed of insulation.

Actuation rod 905 includes a first rod member 911 and a second rod member 912. First rod member 911 includes internal threads 910. A longitudinal slot 913 is formed in an exterior surface of first rod member 911. Second rod member 912 includes external threads 909. A longitudinal slot 914 is formed in an exterior surface of second rod member 912. External threads 909 are configured to engage in a complementary manner with internal threads 910 such that second rod member 912 can be screwed into first rod member 911, for example as seen in FIG. 9E, or out of first rod member 911, for example as seen in FIG. 9E.

Lumen 915 of first shaft member 901 is configured to receive first rod member 911 such that key 907 engages longitudinal slot 913. Lumen 916 is configured to receive second rod member 912 such that key 908 engages longitudinal slot 914. Upon assembly of laparoscopic instrument components 900, for example as seen in FIG. 9B, first rod member 911 is received within first shaft member 901 and second rod member 912 is received within second shaft member 902. External threads 903 are screwed into internal threads 904, and external threads 909 are screwed into internal threads 910. Key 907 engages longitudinal slot 913 and key 908 engages longitudinal slot 914. The engagement between keys 907 and 908 and longitudinal slots 913 and 914 ensures that when first shaft member 901 is rotated relative to second shaft member 902 so as to change the length of shaft 906, first rod member 911 is rotated in a same manner relative to second rod member 912, so as to change the length of rod 905 the same amount as the length of shaft 906 has changed. Moreover, because longitudinal slots 913 and 914 are longer than keys 907 and 908, actuation rod 905 is nevertheless able to translate longitudinally relative to shaft 906 for a distance equal to the length of longitudinal slots 913 and 914, in order to operate an end effector.

Although laparoscopic instrument components 900 have been described above in the context of providing adjustable length insulation for electrosurgical laparoscopic instruments, those skilled in the art will recognize that its length adjustment mechanism is more broadly applicable, for example to adjusting shaft lengths of non-electrosurgical laparoscopic instruments.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A laparoscopic instrument comprising:
a shaft comprising a shaft distal end and a shaft proximal end, the shaft comprising shaft teeth that extend along at least a bottom portion of the shaft;
an actuation rod comprising an actuation rod distal end and an actuation rod proximal end, the actuation rod receivable by the shaft such that the actuation rod will translate longitudinally relative to the shaft to actuate an end effector, the actuation rod comprising actuation rod teeth that extend along at least a bottom portion of the actuation rod, the actuation rod teeth located alongside the shaft teeth with the actuation rod located inside the shaft;

a handle configured to hold the shaft and the actuation rod, the handle configured to cause the actuation rod to translate longitudinally relative to the shaft to actuate the end effector; and a length adjustment mechanism configured to adjust a shaft length, the shaft length defined between the handle and the shaft distal end, the length adjustment mechanism comprising a first gear configured to engage the shaft teeth such that rotation of the first gear translates the shaft longitudinally and a second gear configured to engage the actuation rod teeth such that rotation of the second gear translates the actuation rod longitudinally.

2. The laparoscopic instrument of claim 1, where the length adjustment mechanism is further configured to simultaneously adjust the shaft length and an actuation rod length using the first gear and the second gear simultaneously, the actuation rod length defined longitudinally between the handle and the distal end of the actuation rod.

3. The laparoscopic instrument of claim 1, where the length adjustment mechanism is further configured to adjust the actuation rod length using the second gear without changing an end separation distance, the end separation distance defined longitudinally between the shaft distal end and the actuation rod distal end.

4. The laparoscopic instrument of claim 1, further comprising the end effector, the end effector connected to the shaft distal end and the actuation rod distal end.

5. The laparoscopic instrument of claim 1, further comprising insulation surrounding the shaft, the insulation comprising an insulation length extending along the shaft, the insulation configured to undergo a corresponding change in the insulation length upon an adjustment of the shaft length.

6. The laparoscopic instrument of claim 1, where the length adjustment mechanism comprises a gear mechanism configured to engage each of the shaft, the actuation rod, and the handle.

7. The laparoscopic instrument of claim 1, where:
in a length adjustment configuration, the second gear is configured to be rotated by rotation of the first gear; and
in an end effector actuation configuration, the second gear is configured to be rotated by operation of the handle.

8. The laparoscopic instrument of claim 7, further comprising a control knob connected to the handle, where rotation of the control knob by a user causes rotation of the first gear.

9. The laparoscopic instrument of claim 1, where:
in a length adjustment configuration, the first gear is configured to rotate about an axis of rotation of the first gear; and
in an end effector actuation configuration, the first gear is prevented from rotating about the axis of rotation of the first gear.

10. The laparoscopic instrument of claim 1, where:
the handle comprises a first handle section and a second handle section, the first handle section movable relative to the second handle section; and
the gear mechanism further comprises a gear bracket attached to the first handle section such that, in an end effector actuation configuration, movement of the first handle section relative to the second handle section causes rotation of the gear bracket about the axis of rotation of the first gear.

11. The laparoscopic instrument of claim 10, where rotation of the gear bracket about the axis of rotation of the first gear causes rotation of the second gear.

12. The laparoscopic instrument of claim 10, where:
the second gear is a ring gear; and
the gear mechanism further comprises:
a sun gear configured to engage the first gear; and
a plurality of planet gears each mounted to the gear bracket and configured to engage the second gear and the sun gear.

* * * * *